US006146873A

United States Patent [19]
Kistner et al.

[11] Patent Number: 6,146,873
[45] Date of Patent: Nov. 14, 2000

[54] PRODUCTION OF ORTHOMYXOVIRUSES IN MONKEY KIDNEY CELLS USING PROTEIN-FREE MEDIA

[75] Inventors: Otfried Kistner, Vienna; Noel Barrett, Klosterneuburg/Weidling; Wofgang Mundt; Friedrich Dorner, both of Vienna, all of Austria

[73] Assignee: Baxter Aktiengesellschaft, Vienna, Austria

[21] Appl. No.: 08/849,716

[22] Filed: Oct. 15, 1997

Related U.S. Application Data

[63] Continuation-in-part of application No. 08/487,046, Jun. 7, 1995, Pat. No. 5,753,489, and a continuation-in-part of application No. 08/487,222, Jun. 7, 1995, abandoned, and a continuation-in-part of application No. 08/483,522, Jun. 7, 1995, Pat. No. 5,756,341, and a continuation-in-part of application No. 08/684,729, Jul. 22, 1996, Pat. No. 5,698,433, and a continuation-in-part of application No. 08/338,761, Nov. 10, 1994, abandoned.

[51] Int. Cl.[7] ............................... C12N 7/01; C12N 7/08
[52] U.S. Cl. ...................... 435/235.1; 435/239; 435/237; 435/325; 435/364; 424/93.6; 424/209.1
[58] Field of Search ................................ 435/325, 235.1, 435/237, 239, 364; 424/93.6, 209.1

[56] References Cited

U.S. PATENT DOCUMENTS

| 4,072,565 | 2/1978 | Weiss et al. . |
| 4,205,131 | 5/1980 | Almeida . |
| 4,500,513 | 2/1985 | Brown et al. . |
| 4,525,349 | 6/1985 | Montagnon et al. . |
| 4,664,912 | 5/1987 | Wiktor et al. . |
| 4,783,411 | 11/1988 | Gabliks . |
| 4,927,762 | 5/1990 | Darfler . |
| 5,147,790 | 9/1992 | Wilson . |
| 5,316,938 | 5/1994 | Keen et al. . |
| 5,391,491 | 2/1995 | Mundt et al. . |
| 5,393,668 | 2/1995 | Cinatl et al. . |

FOREIGN PATENT DOCUMENTS

| 0 019 218 | 11/1980 | European Pat. Off. . |
| 0 113 665 | 7/1984 | European Pat. Off. . |
| 0115442A2 | 8/1984 | European Pat. Off. . |
| 0 485 689 | 5/1992 | European Pat. Off. . |
| WO 91/03552 | 3/1991 | WIPO . |
| WO 91/09937 | 7/1991 | WIPO . |
| 96/15231 | 5/1996 | WIPO . |

OTHER PUBLICATIONS

Merten et al., Cytotechnology 14: 47–59 (1994).
Merten et al., Biologicals 23: 185–189 (1995).
Swanson et al., Journal of Biological Standardization 16: 311–320 (1988).
Levenbrook et al., Journal of Biological Standarization 12: 391–398 (1984).
Contreras et al., In Vitro Cellular & Developmental Biology 21(11): 649–652 (1985).
Johnson et al., Develop. biol. Standard. 50: 27–35 (1982).
Katz et al., The Journal of Infectious Diseases 160(2): 191–198 (1989).
Kaverin et al., The Journal of Virology, 68(4): 2700–2703 (1995).
Govorkova et al., The Journal of Infectious Diseases 172: 250–253 (1995).
Bulletin of the World Health Organization 73(4): 431–435 (1995).
Vincent–Falquet et al., Develop. biol. Standard. 70: 153–156 (1989).
Enami et al., Proc. Natl. Acad. Sci. USA 878: 3802–3805 (1990).
Vey et al., Hemagglutinin Activation Of Pathogenic Avian Influenza Viruses of Serotype H7 Requires The Protease Recognition Motif R–X–K/R–R$^1$, *Virology*, vol. 188:408–413, (1992).
Clinatl et al., "Suspension Culture of HeLa Cells In Protein–Free Medium: Sensitivity To Human Pathogenic Viruses", *Intervirology*, vol. 37:361–366, (1994).
Biological Abstracts, vol. 96, (1993), abstract No. 143083, J. Cinatl et al., "Protein–Free Culture Of Vero Cells A Substrate For Replication Of Human Pathogenic Viruses".
Cinatl et al., "Increased HIV–1 Production In Chronically Infected H9 Cells Grown In Protein–Free Medium", *Arch. Virol.*, vol. 125:327–330, (1992).
Luytjes et al., Cell 59: 1107–1113 (1989).
Robertson et al., Journal of General Virology 72: 2671–2677 (1991).
Schild et al., Nature 303: 706–709 (1983).
Klenk et al., "The Molecular Biology of Influenza Virus Pathogenicity", pp. 247–281, Academic Press (1988).
World Health Organization: Technical Report Series, No. 384, pp. 42–56 (1968).
Mayr et al., "Vergleichende Studien über die Züchtung von Geflügelpockenviren in der Zellkultur", pp. 72–102 (1961).
Steineke–Gröber et al., The EMBO Journal, 11:2407–2414 (1992).
Lazarowitz et al., Virology 68:440–454 (1975).
Hirst, Science 94(2437): 22–23 (1941).
Barrett et al., Methods of Immunological Analysis, 2:115–132 (1993).
Scholtissek et al., J. Gen. Virol., 69:2155–2165 (1988).
Barr, Cell, 66:1–3 (1991).
Burnet, Austr. Jnl. Experimental Biology and Medical Science, 18:353–360 (1940).
Tomas et al., Rev. Roum. Med. Virol., 32(2): 145–154 (1981).
Ohuchi et al., J. of Virology 65(7): 3530–3537 (1991).

(List continued on next page.)

*Primary Examiner*—Leon B. Lankford, Jr.
*Attorney, Agent, or Firm*—Foley & Lardner

[57] ABSTRACT

Viruses from the family Orthomyxoviridae, particularly influenza virus, can grown in monkey kidney cells, particularly Vero Cells, after passaging the cells in a serum-free or protein-free medium. The use of a proteolytic enzyme, especially trypsin, also aids in the propagation of the virus. The method allows for the virus to be produced to be used in a vaccine.

37 Claims, No Drawings

OTHER PUBLICATIONS

Boehringer Manneheim Catalog, pp. 191–195 (1994).
Cinatl et al., Biology International 17(9): 885–895 (1993).
Nakamura et al., J. Gen. Virol. 56: 199–202 (1981).
Lau et al., Virology 212: 225–231 (1995).
Estes, Virology, Chapter 48, pp. 1329–1352 (1990).
Barrett et al., Aids Research and Human Retroviruses 5(2): 159–171 (1989).
Kilbourne, Vaccines, Second Edition, Chapter 19, pp. 565–581.

PRODUCTION OF ORTHOMYXOVIRUSES IN MONKEY KIDNEY CELLS USING PROTEIN-FREE MEDIA

This application is a national stage (§ 371) of PCT/EP95/ 04439, Nov. 10, 1996 which is a continuation-in-part of U.S. Ser. No. 08/487,046, filed Jun. 7, 1995 and now U.S. Pat. No. 5,753,489; Ser. No. 08/487,222, filed Jun. 7, 1995 and now abandoned; Ser. No. 08/483,522, filed Jun. 7, 1995 and now U.S. Pat. No. 5,756,341; Ser. No. 08/684,729, filed Jul. 22, 1996 and now U.S. Pat. No. 5,698,433; and Ser. No. 08/338,761, filed Nov. 10, 1994 and now abandoned. Priority is claimed to all of the above application.

FIELD OF THE INVENTION

The present invention concers an approach to propagating a variety of viruses, including virtually any Influenza virus, with comparatively high yields without the need for passaging, including the production of high growth reassortants and attenuated virus. The present invention further provides for the production of vaccines from those viruses. The invention also relates to a cellular biomass that is capable of supporting the cultivation of a diversity of viruses. The present invention also relates to the production of virus, virus antigen and recombinant proteins by the use of that cellular biomass.

BACKGROUND OF THE INVENTION

Efficient vaccine production requires the growth of large quantities of virus produced in high yields from a host system. Different types of virus require different growth conditions in order to obtain acceptable yields. The host in which the virus is grown is therefore of great significance. As a function of the virus type, a virus may be grown in primary tissue culture cells, established cell lines or in embryonated eggs, such as those from chickens.

The cultivation conditions under which a virus strain is grown also are of great significance with respect to achieving an acceptably high yield of the strain. Thus, in order to maximize the yield of a desired virus strain, both the host system and the cultivation conditions must be adapted specifically to provide an environment that is advantageous for the production of a desired virus strain. Therefore, in order to achieve an acceptably high yield of the various virus strains, a system which provides optimum growth conditions for a large number of different viruses is required. Many viruses are restricted to very specific host systems, some of which are very inefficient with regard to virus yields.

Some of the mammalian cells which are used as viral host systems produce virus at high yields, but the tumorigenic nature of such cells invokes regulatory constraints against their use for vaccine production. In fact, the applicable guidelines of the World Health Organization (WHO) indicate that only a few cell lines are allowed for virus vaccine production.

The problems arising from the use of serum in cell culture and/or protein addivites derived from an animal or human source added to the culture medium, i.e. the varying quality and composition of diffent batches and the risk of contamination with mycoplasma, viruses or BSE-agent, are well-known. In general, serum or serum-derived substances like albumin, transferrin or insulin may contain unwanted agents that can contaminate the culture and the biological products produced therefrom. Furthermore, human serum derived additives have to be tested for all known viruses, like hepatitis or HIV, which can be transmitted by serum. Bovine serum and products derived thereform, for example trypsin, bear the risk of BSE-contamination. In addition, all serum-derived products can be contaminated by still unknown agents. Therefore, many attempts are being made to provide efficient host systems and cultivation conditions that do not require serum or other serum derived compounds.

Over time, many viruses change their serotypes. Any change in virus serotype requires a corresponding change in a vaccine intended to elicit immunity toward the new virus serotype. To maintain the efficiency of the protection accorded by a vaccine to a particular new virus serotype, a new vaccine must be produced which confers immunity to that new serotype. To produce the new vaccine, the new virus strains must be grown. Because many viruses, in particular Influenza virus, change serotype very quickly, the cultivation system must be able to produce viral antigen, including virions, in large-scale quantities sufficiently fast to permit production of vaccines during the infection season of the virus.

In many cases, the optimum growth conditions for the new virus strains are different from the conditions employed to grow their predecessors. Accordingly, a cultivation system that can be easily adjusted to provide the requirements for optimum growth of new virus strains is highly desirable. Moreover, practical considerations, such as the need for high production output of the new strain, render highly desirable a method that is applicable to large scale production of the virus, such as influenza.

One typical example of a virus that changes its serotype frequently is Influenza virus. Influenza is a major respiratory disease in man and is responsible for many thousands of deaths every year.

There are three general types of Influenza viruses, Type A, Type B and Type C. The types are defined by the absence of serological crossreactivity between their internal proteins. Influenza Type A viruses are further classified into sub-types based on antigenic differences of their glycoproteins, the hemagglutinin (HA) and neuraminidase (NA) proteins. Humans are susceptible mainly to diseases caused by infection with Influenza Type A, B, and C viruses.

Currently, the most significant causes of Influenza infections in humans are those attributable to Type B and to subtypes H1N1 and H3N2 of Influenza type A. Accordingly, antigens of Type B and of subtypes H1N1 and H3N2 of Influenza Type A are those which are generally incorporated into present Influenza vaccines. The vaccines currently available have protection rates ranging from 75–90%.

The Influenza HA antigen is the major target for the protective immune responses of a host to the virus. One of the problems in the development of effective influenza vaccines stems from the high mutation rate of the gene coding for the HA protein, resulting in frequent changes in its antigenicity. Therefore, in order to produce effective vaccines, new vaccines from recent Influenza isolates must be produced frequently.

The normal practice of recovering new viral isolates involves recovery with a throat swab or similar source, followed by cultivation of the isolates in embryonated chicken eggs. Although the initial isolation into eggs may be difficult, the virus adapts to its egg host, and large scale production of the virus can be carried out in eggs.

Conventional methods for producing influenza vaccine have always involved the growth of the viruses in embryonated chicken eggs. Viruses grown by this method are then used for producing live attenuated virus, killed whole virus or subunit vaccines. However, conventional methodology involving embryonated chicken eggs to produce influenza vaccine is extremely cumbersome, involving the handling of many thousands of eggs per week. In a typical operation, eggs must be candled, the shell must be sterilized and each egg must be inoculated by injection of a small volume of virus into the allantoic cavity. The injected eggs are then incubated for 48–72 hours at 33°–37° C., candled again, refrigerated overnight and opened to allow harvesting of the allantoic fluid. The harvested fluid must then be clarified by filtration and/or centrifugation before processing for further purification. Extensive purification is then required to ensure freedom from egg protein. *Requirements For Inactivated Influenza Vaccine*, World Health Organization Technical Report Series, 384 (1966).

In a typical chicken embryo operation, between one and two eggs are required to produce one dose of influenza vaccine. Thus, to produce a million doses of vaccine, more than a million egg embryos must be processed. In summary, the conventional approach to producing influenza virus vaccines involves many steps which are difficult to automate and are, accordingly, labor intensive, time consuming, expensive and subject to contamination. A need therefore exists for methods which are less labor intensive, require less biological tissue per dose produced and are less susceptible to contamination.

There have been many attempts to adapt standard tissue culture technology with primary chicken embryo cells ("CEC") or established mammalian cell lines for Influenza virus vaccine production. These attempts were unsuccessful because a large number of viral strains do not replicate in conventional cultures. The use of established mammalian cell lines, such as Madin-Darby canine kidney (MDCK) line, has been more successful in replicating some strains. Nevertheless, a number of virus strains will not replicate in the MDCK line. In addition, fears over possible adverse effects associated with employing cells with a tumorigenic potential for human vaccine production have precluded the use of MDCK, a highly transformed cell line, in this context.

One of the primary difficulties in growing a number of influenza strains in primary tissue culture or established cell lines arises from the necessity for proteolytic cleavage activation of the influenza hemagglutinin in the host cell. Cleavage of the virus $HA_0$ precursor into the HA 1 and HA 2 subfragments is a necessary step in order for the virus to infect a new cell. Thus, cleavage is required in order to convert new virus particles in the host cells into virions capable of infecting new cells. Cleavage is known to occur during transport of the integral $HA_0$ membrane protein from the endoplasmic reticulum of the infected cell to the plasma membrane. In the course of transport, hemagglutinin undergoes a series of co- and post-translational modifications including proteolytic cleavage of the precursor HA into the amino-terminal fragment HA 1 and the carboxyterminal HA 2.

The fact that Influenza virions have been found which contain either uncleaved or cleaved HA glycoproteins indicates that cleavage is not always necessary for virus assembly and release from the infected cell. Cleavage of HA is indeed necessary, however, for the initiation of infection of a new host cell.

Although it is known that an uncleaved HA can mediate attachment of the virus to its neuramic acid-containing receptors at the cell surface, it is not capable of the next step in the infectious cycle, which is fusion. It has been reported that exposure of the hydrophobic amino terminus of the HA 2 by cleavage is required so that it can be inserted into the target cell, thereby forming a bridge between virus and target cell membrane. This is followed by fusion of the two membranes and entry of the virus into the target cell.

Proteolytic activation of hemagglutinin follows a pattern observed with many enzymes and hormone precursors, such as proinsulin, progastrin and proopiomelanocortin. It involves cleavage at an arginine residue by a trypsin-like endoprotease. The available evidence suggests that the endoprotease is an intracellular enzyme which is calcium dependent and has a neutral pH optimum. However, beyond these observations, little is known about the nature of the intracellular protease (Klenk et al, "The Molecular Biology of Influenza Virus Pathogenicity", Adv. Virus Res., 34:247–281 (1988)).

Since the activating proteases are cellular enzymes, the infected cell type determines whether the Influenza hemagglutinin is cleaved. The hemagglutinins of the mammalian Influenza viruses and the nonpathogenic avian Influenza viruses are susceptible to proteolytic cleavage only in a restricted number of cell types. On the other hand, the hemagglutinins of pathogenic avian viruses among the H 5 and H 7 subtypes are cleaved by proteases present in a broad range of different host cells. Thus, there are differences in host range resulting from differences in hemagglutinin cleavability which can be correlated with the pathogenic properties of the virus.

The differences in cleavability are due to differences in the amino acid sequence of the cleavage site of the hemagglutinin. Sequence analyses have revealed that the HA1 and HA2 fragments of the hemagglutinin molecule of the nonpathogenic avian and of all mammalian Influenza viruses are linked by a single arginine. In contrast, the pathogenic avian strains have a sequence of several basic amino acids at the cleavage site with the common denominator being lysine-arginine or arginine-arginine. The hemagglutinins of all Influenza viruses are cleaved by the same general mechanism resulting in the elimination of the basic amino acids.

The protease activities which are essential for cleavage of a broad range of influenza virus strains are available in the embryonated egg and in cell aggregates representing the whole chicken embryo. Conventional CEC cultures prepared from chick embryos, however, provide only some of the protease activities of a whole chicken embryo and, hence, allow replication of a limited range of influenza virus strains. Standard procedures for preparation of CEC cultures involve removal of the head and inner organs and multiple trypsinization steps. These procedures result specifically in the loss of brain, heart, lung, liver and kidney cells, which have been shown to replicate a number of influenza strains (Scholtissek et al., *"Multiplication of Influenza A Viruses with Cleavage and Non-cleavable Hemagglutinin in Chicken Embryo Membranes or Organes, and Cell Cultures Derived Therefrom"*, J. Gen. Virol., 69, 2155–2164 (1988). Standard procedures thus result in a highly selected cell population consisting mainly of fibroblasts, which are limited in terms of the virus strains that they can support.

Improvements in influenza virus production have been attempted before. For instance, it has been reported that the limited replication of several Influenza A strains in standard cell cultures could be ameliorated by the addition of trypsin to the tissue culture medium. For example, trypsin addition significantly increases the infectivity of various strains grown in CEC cultures (Lazarowitz et al., "Enhancement of the Infectivity of Influenza and B Viruses by Proteolytic Cleavage of the Hemagglutinin Polypeptide", Virology, 68:440–454 (1975)). In addition Stieneke-Gröber et al., "Influenza Virus Hemagglutinin with Multibasic Site is Activated by Furin, a Subtilisin-like Endoprotease", EMBO J., 11: 2407–2414 (1992), have identified the HA activating enzyme in MDBK cells as a furin-like protease. Such enzymes have been isolated from human and mouse tissues and constitute a new family of eukaryotic subtilisin-like endoproteases.

Other attempts at developing alternative vaccine production methods have been undertaken. U.S. Pat. No. 4,783,411, to Gabliks discusses a method for preparing influenza vaccines in goldfish cell cultures. The virus particles for infecting the Gabliks cultures after their establishment were obtained from chicken embryo cultures or from infected CD-1 strain mice. The virus is passaged at least twice in such goldfish cell cultures, resulting in an attenuated virus which may be used as a live vaccine.

U.S. Pat. No. 4,500,513 to Brown et al. discloses the production of unmodified virus particles for making vaccine from liquid cell culture or cell monolayer culture wherein a protein hydrolyzing enzyme, such as trypsin, chymotrypsin or carboxypeptidase, is incubated with a partially infected culture to increase the proportion of additional cells infected by the virus and to ensure the maximum cytopathic effect. Harvesting of the virus is performed at a point in the growth phase of the virus which exhibits maximum cytopathic effect. All of the examples of Brown, however, describe a dog kidney cell line which is not usable for human vaccine production. Due to the maximum cytopathic effects of the virus in the method according to Brown et al., virus yield is limited to only one round of virus replication. Moreover, Brown does not teach manipulation of the virus genome nor optimization of culture conditions. Therefore, the method of Brown is not applicable for the large-scale production of virus, which is necessary for the efficient production of corresponding vaccines.

U.S. Pat. No. 4,205,131 to Almeida discloses a method for propagating rotavirus in cell culture in the presence of serum-free medium containing the proteolytic enzyme trypsin. Due to the lethal effect on the cells of trypsin at higher levels, the virus yield of Almeida, like Brown, was limited to that produced in one round of replication.

More recently, others have attempted to produce influenza virus in cell-line cultures. For example, Katz et al., J. Infect. Dis. 160:191–98 (1989) has compared the growth characteristics of influenza in MDCK cells and amniotic cavity of embryonated eggs. Katz found that the influenza titer obtained from MDCK cells compared favorably to embryonated eggs. There are problems with using MDCK cells, however. For example, MDCK cells are no licensed cell line for production of human vaccines. Moreover, the Katz procedure requires viruses to be multiply and serially passaged in the MDCK cell line, which is costly and, more importantly, time consuming.

Kaverin et al., J. Virol. 69: 2700–03 (1995) have attempted to grow influenza virus in VERO cells grown in serum-containing medium, VERO cells are licensed by the World Health Organization for general vaccine production.

Kaverin encountered difficulties in propagating influenza virus in VERO cells, however, and linked these difficulties to a loss of trypsin activity in the cell cultures caused by a factor apparently released by the VERO cells. Kaverin addressed this problem by repeatedly adding trypsin, and serial passaging the viruses in the VERO cells. Only after 10 passages in VERO cells did Kaverin obtain a Liter that was as high as could be obtained with embryonated egg and MDCK cells. Similar results were obtained by Govorkova et al., J. Infect. Dis. 172: 250–53 (1995).

Neither Kaverin nor Govorkova address the problems of the use of serum-containing medium, however. Serum-containing mediums generally lack batch-to-batch consistency, and contain undesired contaminants that complicate the viral production and purification process.

These contaminants include contaminating viruses, such as BVDV, Bluetongue virus, prions or BSE, and/or immunogenic proteins, which can present serious safety concerns.

Use of serum-free medium to grow viruses also has been attempted in the prior art. See EP 115442, U.S. Pat. Nos. 4,525,349, 4,664,912. In these methods, the host cells are first grown in serum-containing medium and, just prior to infection with the respective virus, the serum-containing medium is replaced by serum-free medium.

VERO cells have been adapted to growth in serum-free medium, such as MDSS2. Merten et al., Cytotech. 14: 47–59 (1994). MDSS2 lacks growth factors, but still has a significant presence of non-serum proteins (30–40 mg protein/ml). Merten et al., Biologicals 23: 185–89 (1995). Accordingly, MDSS2 is not entirely free of the problems associated with other protein-containing mediums, such as serum-containing mediums.

A continuing need exists for safe and effective methods to produce viruses and their antigen, as well as recombinant proteins in virus-based expression systems. Moreover, there is need for an approach to viral propagation, employing materials that are readily available and requiring a minimal number of time-consuming manipulations, such as adaptation of a virus to a particular cell substrate by serial passaging, that can meet applicable regulatory standards and still accommodate many different viruses and virus strains, especially thoses that can not be multiplied efficiently via conventional methods.

SUMMARY OF THE INVENTION

It is an object of the present invention to provide for the high yield production of viruses from cell culture, and to provide for the production of vaccines from thoses viruses.

It is also an object of the present invention to provide a method for the continuous production of virus from a sustained culture of vertebrate cells, such as CEC or VERO cells, with a minimum of human manipulation.

It is another object of the present invention to provide a method for optimizing the activity of a virus in culture by augmentation with exogenous substances.

It is still another object of the present invention to provide a method for the high yield production of all types of cellular products, that is, viruses or recombinant proteins or other cellular products, in a flexible system that can be easily adapted to the specific requirements of the various products.

It is yet another object of the present invention to provide a cellular biomass that is free of contaminating proteins for the production of biological products, such as viruses, virus antigens or proteins produced by viruses, including recombinant viruses.

It is a further object of the invention to provide a cellular biomass that supports the growth of a large number of different viruses.

It is still a further object of the present invention to provide for the efficient production of virus antigens, including whole virus, from cell culture and to provide for the production of vaccines derived from that virus or virus antigen.

It is yet another object of the present Invention to provide for the production of recombinant proteins free of contaminating proteins derived from the cultivation medium.

In accordance with these and other objects, the present invention provides a method for producing viruses comprising the steps of providing a culture of vertebrate cells, such as VERO cells, growing the cells solely in media that is free of protein (lacking serum and non-serum proteins), infecting the culture with a virus, and incubating the cell culture infected with the virus to propagate the virus into the medium to produce virus-containing medium. Modifications of the method include, is after the step of providing a culture of vertebrate cells and before the step of infecting the cells, that the vertebrate cells are grown in a protein-free medium for at least six generations, preferably for at least twelve generations, more preferably for at least eighteen generations or still more preferably for at least twenty-four generations.

In accordance with another aspect of the present invention, there is provided a method for producing viral antigen, including viruses, comprising the steps of (a) providing a culture of vertebrate cells cultivated solely in protein-free media; (b) infecting the culture with a virus; and (c) incubating said cell culture infected with the virus to propagate the virus. Preferably, the virus is propagated without multiple serial passaging thereof through the culture. The virus can be any type of animal virus, such as those of orthomyxoviridae, paramyxoviridae, reoviridae, picornaviridae, flaviviridae, arenaviridae, herpesviridae, poxviridae and adenoviridae. Preferred viruses include poliovirus, HAV, TBEV, yellow fever virus, rubella virus, HCV, mumps virus, measles virus, respiratory syncytial virus, influenza virus, lassa virus, junin virus, reovirus type 3, adenovirus type 1 to type 47, HSV 1, HSV 2, CMV, VZV, EBV, rotavirus and vaccinia virus. More preferably, the virus is an influenza virus, such as influenza A, B and C. The cells used to propagate the virus include VERO cells, CV-1 cells, LLC-MK2 cells, MDCK cells, MDBK, WI-38 and MRC-5 cells. Preferably, the cells are VERO cells in a cellular biomass.

In accordance with another aspect of the invention, the method further comprises the steps of (d) removing a portion of the cell culture of step (c); (e) contacting the portion of step (d) with at least one substance that augments the activation of the virus; (f) adding to the portion of step (e) at least one compound which inhibits or attenuates any cell toxic effects of the substance; and (g) returning the portion of step (f) to the culture. Preferably, the substance that augments the activation of said virus is a protease. The substance that augments the activation of the virus is preferably a protease that cleaves a glycoprotein responsible for fusion of virus and host cell membrane. Where the virus being propagated is influenza, the protease cleaves Influenza hemagglutinin. Preferably, the protease is from a prokaryotic source, such as pronase, thermolysin, subtilsin A or a recombinant protease.

In accordance with another aspect of the present invention, there is provided a cellular biomass comprising vertebrate cells cultivated solely under protein-free conditions, wherein said cellular biomass sustains propagation of viruses without serial passaging thereof through said cells. The cellular biomass can be obtained by growing cells on a carrier in a protein-free medium.

In accordance with still another aspect of the present invention, there is provided a method of producing a cellular biomass, comprising the steps of: (a) growing cells under solely protein-free conditions in a vessel containing a carrier and protein-free medium such that the cells grow on said carrier and form a biomass attached to the carrier; and (b) contacting the cellular biomass and the carrier with a substance to separate the cellular biomass from the carrier. Preferably, the substance is a protease. The protease is preferably derived from a prokaryot, such as thermolysin, subtilisin A or pronase.

In accordance with still another aspect of the present invention, there is provided a method of producing a donor virus from segmented viruses such as Orthomyxoviruses, for making reassortant viruses, comprising the steps of: (a) growing a culture of vertebrate cells solely in protein-free medium; (b) infecting the culture with a virus; (c) incubating the cell culture infected with the virus; (d) selecting for a virus strain that exhibits a desired phenotype in vertebrate cells; and (e) isolating the donor virus from step (d). Preferably, the virus is an Influenza virus and the desired phenotype is a high-yield phenotype or an attenuated virulence phenotype. The virus of step (c) can include attenuated Influenza viruses, cold-adapted Influenza viruses, temperature-sensitive Influenza viruses, reassortant Influenza viruses, high yield donor Influenza viruses, wild-type Influenza viruses isolated from throat swabs of infected mammals and viruses that have been passaged in embryonated chicken eggs or cell culture adapted strains of Influenza viruses. The cells to propagate the viruses can include VERO cells, CV-1 cells, LLC-MK2 cells, MDCK cells, MDBK cells, WI-38 and MRC-5 cells. One preferred donor virus obtainable according to the invention is A/Orth/17/95 (H1N1), which exhibits a high-yield phenotype in VERO cells.

In accordance with yet another aspect of the present invention, there is provided a method of producing a reassortant Orthomyxovirus virus, comprising the steps of: (a) co-infecting a vertebrate cell culture in protein-free medium with a first Orthomyxovirus having a desired phenotype, such as a high-yield and/or an attenuated virulence phenotype, and a second Orthomyxovirus having at least one antigenic determinant of the current vaccine strain; incubating the vertebrate cell culture of step (a) to propagate the viruses and reassortants of said viruses, (c) selecting from said co-infected culture a reassortant virus that comprises the desired phenotype, such as a high-yield and/or attenuated virulence phenotype, of the first Orthomyxovirus and at least one antigenic determinant of said second orthomyxovirus. Preferably, the Orthomyxovirus viruses are Influenza viruses.

Step (c) can employ an antibody that binds to antigenic determinants of the first Orthomyxovirus but does not bind to antigenic determinants of the second Orthomyxovirus. Preferably, the second Orthomyxovirus is designated for vaccine production.

In one preferred embodiment the reassortant Orthomyxovirus is produced in a biomass of VERO cells.

In accordance with yet another aspect of the present invention, there is provided an antibody for selecting reassortant viruses for vaccine production, wherein the antibody binds to antigenic determinants of a donor virus but do not bind to antigenic determinants of a virus designated for vaccine production. Preferably, the antibody binds to outer surface glycoproteins, such as hemagglutinin and neuraminidase, of the donor virus.

The present invention also provides an improved method of making viral antigen, including viruses, by employing the steps of removing a portion of the virus-containing medium, contacting the portion with at least one substance which augments the activation of the virus for a sufficient amount of time for the activation to occur, then adding to the removed portion one or more compounds which inhibit or attenuate any of the cell toxic effects of the at least one or more substances for a sufficient amount of time for the inhibition or attenuation to occur, and then returning the portion to the cell culture. Suitable vertebrate cells for use with the invention include chicken embryo culture cells, VERO cells, CV-1 cells, LLC-MK2 cells, MDCK cells and MDBK cells, as well as vertebrate cell aggregates comprising a plurality of cell types.

The viral antigens, including viruses, produced according to the invention include the antigens of Orthomyxoviridae, Paramyxoviridae and Reoviridae, and preferably is an Influenza virus. The substance that augments the activation of the virus is preferably a protease that cleaves a glycoprotein responsible for fusion of virus and host cell membrane such as a protease that cleaves Influenza hemagglutinin. Suitable proteases may be selected from the group consisting of the trypsin family and the family of subtilisin-like enzymes. More specifically, the protease may be selected from the group consisting of trypsin, chymotrypsin, thermolysin, pronase, subtilisin A, elastase, pepsin, pancreatin, carboxypeptidase and furin. Most preferred protease is a protease derived from a prokaryotic source, such as pronase, subtilisin A or thermolysin.

The method according to invention also can have the substance that augments viral activation in a vessel or immobilized on a carrier.

In one specific embodiment the Influenza virus has been altered to modify a cleavage site or to create a new cleavage site in the glycoprotein. When the method is applied to Influenza virus, the hemagglutinin of the Influenza virus is preferably altered to contain the cleavage site of amino acids KKRKKR. The invention also can include the use of a compound that inhibits, attenuates or removes any cell toxic effects of the activating substance, such as soybean trypsin inhibitor, egg trypsin inhibitor and aprotinin. Preferably, said inhibitors are provided an a vessel or immobilized on a carrier.

The method of the invention also can include the steps of monitoring the growth, infection and activation levels of the culture, for varying the conditions of the culture to maximize growth, infection and activation levels, for harvesting the virus from the culture, and for preparing a vaccine with the harvested virus. The method of the invention provides further for the treatment of Influenza virus infection or for the prevention of Influenza virus infection by administering to an animal a vaccine obtainable by the methods described above.

The method of the invention also can include the steps of augmenting or optimizing the production of viral antigen, including viruses, comprising the steps of providing a cell culture of vertebrate cells, growing the cells in protein-free medium, infecting the cell culture with a virus, incubating the cell culture infected with the virus to propagate the virus into the medium to produce a virus-containing medium, removing a portion of the virus-containing medium, contacting the portion with at least one substance which augments the activation of the virus, adding to the portion, at least one compound which inhibits, attenuates or removes the cell toxic effects of the one or more substances that augment the activation of the virus, and returning the removed virus-containing medium portion to the cell culture and medium.

The method of the invention also can include the steps of providing, growing, infecting and incubating optionally are performed in a first vessel and the steps of contacting and adding are performed in a second vessel and further that the first and second vessels are connected in a loop so that steps of providing, growing, infecting, incubating, removing, contacting, adding and returning can be performed in a closed cycle or the like.

Other options within the scope of the invention include the steps of providing, growing, infecting and incubating are performed in a first vessel, the step of contacting is performed in a second vessel, and the step of adding is performed in a third vessel and, optionally, wherein the first vessel, the second vessel and the third vessel are connected in a loop so that all of the steps can be performed in a batchwise manner, cyclic manner or the like.

The invention can, be practiced with a variety of vertebrate cell types. For example, vertebrate cells of the method may comprise a plurality of cell types or those chosen from chicken embryo cell cultures, VERO cells, CV-1 cells, LLC-MK2 cells, MDCK cells, MDBK cells, WI-38 and MRC-5 cells.

In one preferred form of the invention, the virus may be an Influenza virus and the cells to be infected are VERO cells that have been grown from the start in a protein-free mediums. A substance to activate the virus is added, such as a protease that cleaves Influenza hemagglutinin, which can be one or more proteases selected from the trypsin family or the family of subtilisin-like enzymes selected from the group of trypsin, chymotrypsin, thermolysin, pronase, subtilisin A, elastase, pepsin, pancreatin, carboxypeptidase and furin. Most preferred protease is a protease derived from a prokaryotic source, such as pronase, subtilisin A or thermolysin.

The method of the invention also can include the steps of monitoring the growth, infection and activation levels of the culture, and as well as for varying the conditions of the culture to maximize the growth, infection and activation levels of the cells and virus, and for harvesting the virus from the culture, preparing a vaccine with the harvested virus, and for the treatment of Influenza virus infection and for the prevention of Influenza virus infection by administering to an animal a vaccine obtained by the method.

The method of the invention also can include the steps of optimizing the production of one or more products of cultured cells, comprising the steps of providing cells in culture in a first vessel, transferring a portion of the cells to a second vessel, activating the portion of the cells in the second vessel by the addition of one or more substances to optimize the production of a desired product, transferring the portion of the cells to a third vessel, adding compounds to the portion of the cells in the third vessel which attenuate the cell toxic effects of the one or more exogenous substances, wherein the first, second and third vessels are connected in a circular loop system or the like, returning the portion of the cells to the first vessel. The method provides also for batchwise or continuous production, for effecting processing of a portion of the culture can include substantially all of the cells in the culture, and for culturing the cells and virus in a culture medium that provides optimum conditions for cellular growth and production.

The method of the invention also can include controlling, such as increasing, the infectivity of viruses that express a protein involved in activation of the virus, comprising the steps of providing a culture of vertebrate cells, growing the cells in protein-free medium, infecting the culture with a virus that has a modified cleavage site in the protein involved in activation of the virus, wherein the modified cleavage site increases the susceptibility of the virus to the cleavage enzymes in a culture of vertebrate cells, and incubating the cell culture infected with the virus to propagate the virus and to produce virus-containing medium. The method is particularly useful wherein the virus is an Influenza virus that has been altered to modify a cleavage site in its hemagglutinin or to create a new cleavage site, preferably KKRKKR or the like, in its hemagglutinin, and wherein the vertebrate cells are chosen from chicken embryo culture cells, VERO cells, CV-1 cells, LLC-MK2 cells, MDCK cells and MDBK cells as well as vertebrate cell aggregates comprising a plurality of cell types.

The aspect of the invention pertaining to increasing the infectivity of a virus also may comprise the steps of removing a portion of the medium containing the virus, contacting the portion with at least one substance which augments the activation of the virus, adding to the virus-containing portion at least one compound which inhibits, attenuates or removes the cell toxic effects of the one or more substances that augment the activation of the virus, and returning the removed portion to the cell culture and medium. Preferred substances which augment the activation of the virus are proteases which activate a protein involved in virus activation, for example, those which cleave Influenza hemagglutinin which include the proteases selected from the trypsin family or the family of subtilisin-like enzymes, preferably selected from the group of trypsin, chymotrypsin, thermolysin, pronase, subtilisin A, elastase, pepsin, pancreatin, carboxypeptidase, and furin. Most preferred protease is a protease derived from a prokaryotic source, such as pronase, subtilisin A or thermolysin.

An accordance with yet another aspect of the invention there is provided a cultivated virus free of contaminating protein derived from the cultivation medium, such as a protein derived from human or animal sources, such as pig, cattle, sheep and chicken (egg) or a protein being a pathogenic agent.

In yet another aspect of the invention there is provided a virus antigen free of contaminating protein derived from the cultivation medium, such as a protein derived from human or animal sources, such as pig, cattle, sheep and ckicken (egg) or a protein being a pathogenic agent. The virus or virus antigen is preferably derived from TBEV, HAV, HSV, Parvovirus or Influenza virus.

In accordance in another aspect of the invention there is provided a vaccine comprising a virus antigen free of contaminating protein derived from the cultivation medium, such as a protein derived from human or animal sources, such as pig, cattle, sheep and ckicken (egg) or a protein being a pathogenic agent. The virus can be an attenuated virus or may be inactivated. Preferably, the vaccine comprises in addition to the virus antigen a pharmaceutically acceptable carrier. The vaccine can be applicated to a mammal parenterally or orally. The virus antigen is preferably used for the preparation of a vaccine for the treatment or prevention of a mammal against virus infection.

In yet another aspect of the invention there is provided a method for producing a recombinant protein comprising the steps of (a) providing a culture of vertebrate cells cultivated solely in protein free media; (b) infecting said cell culture with a viral vector expressing a recombinant protein; (c) incubating said cell culture infected with said viral vector to propagte said virus; and (d) recovering said recombinant protein. The viral vector is preferably a vaccinia virus. The recombinant protein expressed by that viral vector is selected from the group consisting of viral proteins, bacterial proteins and blood factors.

DETAILED DESCRIPTION OF THE PREFERRED EMBODIMENTS

The present invention provides a new system for the production of biological produces such as viruses, virus antigens or recombinant proteins derived from a viral expression vector. A new methodology has been developed for preparing vertebrate cellular biomass that can be used for large scale production of biological products exhibiting increased safety with regard to unwanted contaminants. The "cellular biomass" of the invention comprises vertebrate cells cultured under protein-free conditions, including the absence of serum proteins. The need for serial passaging of viruses through cells is avoided by using cells from a protein-free environment.

The term "protein-free" as used herein refers to the absence of protein, serum and non-serum proteins alike, in a given context. For example, a "protein-free" medium would be free of proteins, and can be made from minimal essential mediums such as DMEM or DMEM HAM'S F12. A "protein-free" culture would include cells growing in a protein-free medium, and "protein-free" conditions would refer to growing cells in a protein-free medium. Such a culture would contain proteins from the cells and, optionally, any proteins specifically added. Accordingly, in the context of a protein-free culture of cells, the culture would contain desired proteins, such as cell-originated proteins and any added proteins, but would not contain unwanted proteins from protein-containing mediums, such as the proteins in MDSS2.

Preferably, the cells are grown from the original ampoule to the cellular Biomass solely under protein-free conditions. The cultivation medium is preferably composed of a synthetic minimal medium and yeast extract and a derivative of a cyclodextrin, such as $\alpha$-cyclodextrin, $\beta$-cyclodextrin, $\gamma$-cyclodextrin, 2-hydroxypropyl-$\beta$-cyclodextrin, methyl-$\beta$-cyclodextrin, di-methyl-$\beta$-cyclodextrin or tri-methyl-$\beta$-cyclodextrin. Preferably, following the receipt of cell lines from culture collections or other sources where they may have been cultivated in serum containing medium they are subsequently maintained i-n protein-free growth conditions for a number of generations sufficient to ensure the complete lack of proteins as well as a high yield of virus. Thus, according to the present method, growth of mammalian cells under protein-free cultivation conditions occurs for multiple generations, preferably for at least six cell generations, more preferably for at least twelve cell generations, even more preferably for at least eighteen cell generations and still more preferably for at least twenty-four cell generations before infection with a virus.

The present invention also provides a cellular biomass that grows under protein-free conditions from the original ampoule or cell line to a large-scale cellular biomass. A cellular biomass includes cells in culture and aggregates of cells, including cells attached to carriers that, surprisingly, achieve a greater density than cells grown in protein-containing mediums. The cellular biomass according to the invention does not need any adaptation phase to protein-free culture conditions. Cells obtained from a culture collection such as ATCC or WHO are obtained in serum-containing medium but can be immediately transferred to protein-free conditions without any adaptation process.

The use of the cellular biomass according to the invention represents a great improvement over the prior art, because no time is lost due to the lack of an adaptation by the cells. The number of generations of the cellular biomass that must be grown before infection is not higher than the number needed for cell cultures grown in the presence of serum. After an extensive number of generations of growth, usually between 100 and about 300 generations, certain transformed cells lines become tumorigenic. Thus, the present invention combines the advantage of providing a cellular biomass free of any contaminating compound derived from the cultivation medium or subculturing procedures with the advantage of avoiding the risk of tumorigenicity caused by the need for extensive generational growth.

In addition, the present system provides a cellular biomass that has a surprisingly increased cell density compared to cells grown in serum-containing cultivation medium. Due to the higher cell density of the cellular biomass, a more economic production process for biological products is provided.

In a preferred embodiment of the invention, the cells are grown on carriers, which include various insoluble substrates such as microcarriers. A cellular biomass comprising cells attached to a microcarrier is used in large scale fermentation systems. The cells attached to microcarriers grow in multilayers on the carrier and the cells do not detach from the carrier under protein-free cultivation conditions. This is a remarkable and unexpected finding since prior art reports the detachment of cells from the supporting carrier followed by the formation of clumps and cell aggregates.

Suitable vertebrate cells for use of preparing a cellular biomass of the present invention are anchorage-dependent cells, including cells selected from the group of VERO, CV-1, LLC-MK-2, MDCK, MDBK, MRC-5 and WI-38. The cells of the cellular biomass are bound directly or indirectly to a carrier. Glass, cross-linked dextran, gelatine or synthetic material has proven to be well suited as the material for the carrier. A microcarrier whose particle diameter is in the range between 100 $\mu$m and 3000 $\mu$m has proven very efficient in the context of the present invention. The microcarrier may have a smooth surface or a porous structure. In a preferred embodiment of the invention the cellular biomass is derived from an African green monkey kidney cell line, preferably a VERO cell line.

The cellular biomass of the present invention is obtained by the use of an inexpensive, synthetic medium that contains no protein derived from a human or an animal sources, such as pig, cattle, sheep, goat or chicken (egg). The medium used according to the invention ensures a high quality with regard to safety standards. In addition, the present invention provides for an increased cell density per gram of microcarrier. The invention results in an increased production efficiency of biological products. In addition, a reduced quantity of microcarrier is needed for the production process.

In a further aspect, the cellular biomass of the invention allows the efficient virus production and high yield production of different viruses and, in one preferred embodiment, of all types and strains of influenza virus. The present invention allows viral propagation on the cellular biomass that gives similar or even greater yields than serum-containing cell cultures infected with the same virus. Surprisingly, viruses that did not propagate in prior art cell cultures, such as influenza A, B and C show efficient virus replication and propagation on the cellular biomass of the present invention. In addition, viruses, in particular Influenza virus, that did not propagate on serum-derived cell cultures, propagate on the cellular biomass of the present invention. It was highly unexpected that viruses that did not propagate on conventional cell cultures gave rise to efficient virus production with the cellular biomass of the invention.

The biomass of the present invention provides an inexpensive and easy-to-prepare system for the large scale production of a cell culture. In addition, the present system allows the use of an identical growth scheme for a cell line at any time as it cannot be guaranteed for the cell production under serum-containing conditions. The biomass provided can be used in large scale fermentation systems of at least 500 liters. By virtue of its flexibility, the system can be adapted for the production of virus, virus antigen or recombinant products.

In addition, if the present system is used for the production of biological products, such as vaccines or pharmaceutical products, purification steps to remove contaminants derived from the medium can be reduced or eliminated. It is well known in the art, that serum components are attached to proteins, viruses or virus antigens produced in a cell culture. By using a medium free of protein components to prepare a cellular biomass, time consuming purifications steps can be avoided. Additionally, processes performed to inactivate potential contaminating agents, such as BSE, bovine diarrheal virus or bluetongue virus, are sometimes very harsh and thus have negative effects on the biological activity of the product obtained. The cellular biomass of the present invention can produce a biological product that is devoid of a contaminating agent derived from the culture medium.

The biological product obtained by the use of the cellular biomass of the invention is easier to purify and safer with regard to potential pathogenic agents derived from the culture medium or culture medium additives.

The cellular biomass of the present invention represents the most economical means for fulfilling the criteria of providing a safe, quality-ensured cell culture system for the production of safe biologicals.

The present invention also provides for a method for the production of a cellular biomass comprising the steps of providing an original vertebrate cell line or primary cell culture and cultivate the cell line or culture in protein-free medium to prepare a master cell bank. The original cell line can be obtained from the American Type Culture Collection ("ATCC"), WHO or any institute that provides cell lines accepted for the production of biologicals that are used for an application to humans. The original cell line may also be a new cell line that fulfills all criteria set by the WHO for large scale production of biological products. The original cell line is cultivated in the protein free medium without the need of further adaptation to that medium. Subculturing methods can be performed in a manner similar to that used with conventional serum-containing conditions, with the exception that for the subculturing steps a protease derived from a prokaryotic source, such as pronase, thermolysin or subtilisin A is used. The cellular biomass of the invention, therefore, is safe with respect to the risks associated with the use of a eukaryotic protease, such as trypsin.

Certain viruses require an activation step for propagation. These viruses include those of the orthomyxoviridae family, such as Influenza viruses A, B and C, those of the paramyxoviridae family, such as parainfluenza virus Types 1, 2, 3 and 4 or Newcastle Disease virus, and those of the reoviridae family, for example, rotavirus Types A, B and C. Activation of these viruses involves a proteolytic cleavage reaction.

For growth of influenza virus, activation is preferably conducted with a protease from a prokaryotic source, such as pronase, thermolysin or subtilisin A, instead of a protease derived from a eukaryotic source. The method can also comprise the step of preparing a working cell bank from the master cell bank by allowing additional growth in protein-free medium.

The invention also can include the steps of providing a cellular biomass as described in detail above, infecting the cellular biomass with a virus and incubating the biomass infected with that virus under protein-free conditions.

Preferably, the cellular biomass is derived from cells grown for generations in protein-free mediums. Suitable vertebrate cells of the biomass are anchorage-dependent cells, including cells selected from the group of VERO, CV-1, LLC-MK-2, MDCK, MDBK, MRC-5 and WI-38, preferably such derived from an African green monkey kidney cell line, most preferably from a VERO cell line. The cellular biomass is infected with the virus under standard conditions and the cellular biomass infected with that virus is cultivated under standard conditions, with the exception that protein-free medium is used. Cell growth, infection and virus production is monitored periodically. The monitoring can be by automated or other means and results of the monitoring can be used to control the production process.

By infecting and incubating the cellular biomass with the virus, a cell culture is obtained comprising virus-containing supernatant and/or a cellular biomass comprising virus and virus antigen. Dependent on the nature of the virus used, the virus particles produced are either found in the supernatant of the cell culture and/or are associated with the cellular biomass.

Examples for lytic viruses include influenza virus and vaccinia virus and for non-lytic viruses, TBEV. The virus produced and released in the cell culture medium is separated from the cellular biomass by conventional methods, such as centrifugation or ultrafiltration, and harvested.

During infection and propagation not all virus particles produced by the cell are released in the supernatant. Rather, these particles are still associated with the cells of the cellular biomass. Therefore, the cell culture contains virus particles in the supernatant and complete virus particles as well as virus proteins associated with the cellular biomass. To obtain an increased virus yield, the virus particles from the supernatant are harvested and the virus and/or virus antigen associated with the cellular biomass are isolated. The virus found in the cells of the cellular biomass is released from the cells by lysis. The cells can be lysed by conventional methods, such as treating the cells with a detergent, treating with heat, sonication, French-press or other cell lysing methods. The viruses released from the cells are harvested, concentrated and purified.

Viral antigens still associated with the cellular biomass or with cell fragments can be extracted from the cells or cell fragments by chemical or mechanical methods known in the art. These methods include ultrasonication or treatment with an appropriate detergent to release the virus antigen from the cell or cell fragments, especially from the membrane. The virus antigen, including viruses, isolated from the cellular biomass, then, can be further subjected to a purification step including separation on a sucrose-gradient, adsorption to a chromatography column, washing and eluting the purified virus or virus antigen. The chromatography column used is selected from ion-exchange chromatography, affinity-chromatography or size filtration chromatography.

Furthermore, the invention can comprise the step of separating the virus from the cellular biomass, harvesting the virus from the supernatant, purifying the virus and preparing a vaccine with the virus. The method also can comprise the step of releasing intracellular virus from the cells of the cellular biomass, isolating and purifying the virus and preparing a vaccine of the virus. Additionally, the invention can comprise the steps of extracting a virus antigen associated with the cells or cell fragments of the cellular biomass, separating the virus antigen from the cellular biomass, isolating the virus antigen, purifying the antigen and preparing a vaccine with the antigen.

The method provided by the present invention can combine a cellular biomass and a product production process, wherein all steps are performed under protein-free conditions with an increased accessibility of different viruses to the cellular biomass and an improved method for obtaining virus and virus antigen from the same cellular biomass. By this method, maximum virus and virus antigen yields are obtained employing this cellular biomass and this production process.

In one preferred embodiment of the invention, the cellular biomass is derived from VERO, CV-1 or LLC-MK2 cells and the virus is influenza virus, TBEV, HSV, HAV, CMV or vaccinia virus.

Examples of viruses that can be used for the invention are those of the group consisting of the virus families of orthomyxoviridae, paramyxoviridae, reoviridae, picornaviridae, flaviviridae, arenaviridae, herpesviridae, poxviridae and adenoviridae, preferably those selected from the group consisting of poliovirus, HAV, TBEV, yellow fever virus, rubella virus, HCV, mumps virus, measles virus, respiratory syncytial virus, influenza virus, lassa virus, junin virus, reovirus type 3, adenovirus type 1 to type 47, HSV 1, HSV 2, CMV, VZV, EBV, rotavirus and vaccinia virus.

Recombinant viral vectors comprising a foreign nucleic acid to be expressed under the control of a transcriptional and a translational element also can be grown according to the present invention. The viral vector can be an adenovirus vector or a poxvirus vector, preferably a vaccinia virus vector. The foreign nucleic acid inserted into the viral vector can encode a recombinant protein, such as viral proteins, preferably antigens, bacterial proteins and blood factors. Preferred viral antigens are those of HIV, such as gp160 or gp120, those of HBV, such as HBsAg, preS2 or preS1, those of HCV, those of parvovirus, those of HAV, those of TBEV, such as prM/M or E, those of influenza virus, such as HA or NA. Preferred bacterial antigens are those selected from Borrelia, Pseudomonas and Haemophilus influenzae. Preferred blood factors include Factor II, Factor V, Factor VII, Factor VIII, Factor IX, Factor X, Factor XIII, Protein C, Protein S, von Willebrand Factor and antithrombin III.

In a preferred embodiment of the invention, the cellular biomass is derived from VERO, CV-1 or LLC-MK2 cells and the virus is Influenza virus. The use of a cellular biomass that is derived from cells grown for generations under protein-free conditions has not been described in the prior art. With the present invention, the production of all strains of Influenza virus in cell lines like VERO, CV-1, LLC-MK2 has become possible. Surprisingly, it has been found that Influenza strains propagate on the cellular biomass of the invention, whereas no or little propagation was found on conventional serum-containing cell cultures.

As described above, Influenza virus infectivity often depends upon an activation step. The activation of Influenza virus is the result of the activity of a cellular protease that cleaves Influenza hemagglutinin (HA). Since it was found that several Influenza strains propagate on the cellular biomass of the present invention but not on conventional cell cultures, the cellular biomass of the invention provides an active protease that is responsible for increased infectivity of influenza virus and that is not available in conventional cell cultures. An activating substance, such as a protease, can be used with the cellular biomass according to the invention. Activation can be achieved by addition of extraneous proteases derived from a prokaryotic source, such as subtilisin A, pronase or thermolysin or a protease that is produced by recombinant techniques.

In addition, the invention provides for the use of the protease at much higher concentrations than those normally tolerated by culture cells, thereby further increasing the level of HA activation.

This increase in infectivity is achieved by the use of an "augmentation loop", whereby portions of virus-containing medium, cells or both from a cell fermentor containing cells cultured and infected according to the present invention are periodically or continually removed to a vessel or a column containing one or more proteases, such as subtilisin A or pronase. After a certain incubation time, the removed medium, cells or both are transferred to a vessel containing a substance which inhibits the protease activity, and the medium is subsequently returned to the cell-containing fermentor. The augmentation loop aspect of the invention is adaptable also to optimizing parameters of cell growth or output such as to increase the production of a particular protein or virus.

In accordance with another aspect of the invention, a virus is provided that is free of a contaminating compound derived from the culture medium.

In another preferred embodiment of the invention, there is provided a virus antigen that is free of a contaminating compound derived from the culture medium. These contaminating compounds include those derived from human or animal sources, such as pig, cattle, sheep, goat or chicken (egg) or a protein being a pathogenic agent.

The cellular biomass used for the virus production is derived from cells that are grown under protein free conditions and passaged and subcultured with a protease derived from a prokaryotic source. During the infection and virus production processes, no other additives are used, than those employed during the biomass production process. This process, herewith, ensures that the biological product derived from the production process is free of any contaminating compound derived from human or animal sources, such as pig, cattle, sheep, goat or chicken (egg) or a protein being a pathogenic agent.

In accordance with another aspect of the invention, there is provided a virus vaccine comprising a virus or a virus antigen that is free of any contaminating compound derived human or animal sources, such as pig, cattle, sheep, goat or chicken (egg). This virus can be an attenuated virus or may be inactivated. The viral antigen is used for the prepartion of a vaccine for the treatment and prevention of virus infections. Preferred virus antigens for the vaccine preparation are thoses derived from TBEV, HAV, HSV or Influenza virus.

The present invention also permits control of the variants ultimately propagated. For example, Influenza vaccine virus, as it is commonly produced in embryonated chicken eggs, does not fully replicate the original virus taken from the infected patient. Not only does production of virus in eggs allow the accumulation of multiple mutations during virus propagation, it also selects for egg-specific variants that may never arise in a mammalian population. This is one major reason for the poor efficiency of some Influenza virus vaccines:

The present invention provides efficient methods for transferring Influenza virus strains directly from the infected mammal into a vertebrate cell culture and for the high yield propagation of the virus while eliminating the disadvantages of procedures performed in embryonated chicken eggs. The present invention also eliminates the risk of selecting for egg-specific variants that do not contain the appropriate antigenicities for the virus strains of a current Influenza epidemic as well as eliminates the risks attendant to egg material contaminants in vaccine preparations.

One important aspect of the method of the present invention is its flexibility with regard to the strains of virus that can be produced at high yield. In particular, the present invention provides methods for the production of any type of Influenza virus in heretofore unknown high yields. The present method is useful with respect to any Influenza strain that already exists or an Influenza strain that may arise in the future. The method provided by the present invention is adaptable to any possible requirement of an Influenza virus.

In one preferred embodiment, the method provided by the present invention comprises the periodic or continuous removal of "treatment portions" of the virus-containing culture medium from the culture vessel into an "augmentation loop" and the subsequent return of the Treatment portions to the culture vessel. In the augmentation loop, the treatment portion is subjected to exposure to one or more substances which increase the infectivity of the virus. The term "substances" refers to proteases of natural or synthetic origin, including homologs, analogs, muteins, mimetics, pro-enzymes and fragments of proteases. Other compounds which can effect activation, typically by proteolytic cleavage, are also within the scope of the present invention and are thus "substances". For example, high concentrations of proteases that augment the activation of the virus, such as trypsin or subtilisin A, can be introduced into the treatment portion. The proteases can be then neutralized, inhibited or removed and the treatment portion returned to the culture vessel. Thus, the positive effects of the proteases on the virus are realized while the negative effects of the proteases on the culture are reduced or eliminated. As one consequence, the method of the present invention allows high yield production of virus that can be readily scaled up to large scale production rates. Until now, methods that employed proteases for viral activation were not applicable for the large scale production of virus, since the removal of proteases by repeated washes is virtually impossible to perform with large fermentors.

The 'augmentation loop' aspect of the present invention allows use of a proteolytic enzymes at much higher concentrations than those normally tolerated by cells in culture, thereby increasing the level of viral activation, for example the cleavage of HA, while eliminating substantially the toxic effects of protease on the cells. This advantageous aspect is achieved by use of a system, whereby a portion of virus-containing medium from a cell fermentation vessel is removed to a second location such as a column, tube, pipe, manifold, reaction flask or other type of second vessel, and contacted therein with a protease or substances which augment the activation of the virus. After an incubation period sufficient to activate the virus, the removed portion is transferred to a third location such as a column, tube, pipe, manifold, reaction flask or other type of second vessel, and contacted therein with protease inhibitor or compounds which inhibit or attenuate the cell toxic effects of the proteases or substances that augment the activation of the virus. After an incubation period sufficient to inhibit or attenuate the cell toxic effects of the proteases or substances that augment the activation of the virus, the removed portion is returned to the cell fermentation vessel.

The present invention also includes the aspect of altering the susceptibility of a virus strain to trypsin or other proteolytic enzymes in order to ensure the efficient production of new virus strains which cannot be activated by standard methodologies. The specific concepts underlying the claimed invention have not been recognized prior to the present invention.

In the augmentation loop aspect of the present invention, high concentrations of exogenous enzymes can indeed be utilized to augment virus activation in protein-free vertebrate cell lines as well as in CEC cultures. Specifically, following incubation of media containing infected cells and virus, the protease or other enzymes are neutralized or removed at intervals by protease inhibitors or by inhibitors for the enzyme used such as immobilized antibodies which can bind to a protease. This aspect of the invention allows a higher degree of activation compared to other methods which employ lower concentrations of trypsin and, because the present method provides that the trypsin is neutralized or removed at regular intervals, allows continuous production and harvesting of the virus rather than batch production and a single harvest. Most importantly, the present invention provides a method that can easily be scaled up to large scale fermentation for the high yield production of Influenza and other viruses.

To allow the high yield production of all types of viruses, including all strains of Influenza virus, the present invention provides a method for efficient virus production in vertebrate cells. Being primarily designed for the high yield production of Influenza virus, the method of the present invention can be used for the high yield production of any virus that requires substances, such as proteases, that are harmful to cellular hosts.

Examples of viruses that require an activation step are those of the orthomyxoviridae family, such as Influenza viruses A, B and C, those of the paramyxoviridae family, such as parainfluenza virus Types 1, 2, 3 and 4 or Newcastle Disease virus, and those of the reoviridae family, for example, rotavirus Types A, B and C. Activation of these viruses involves proteolysis.

For further augmentation of virus production levels, the inventors provide the optional method of treating the virus producing cell culture with one or more substances, that cleave Influenza hemagglutinin thereby rendering the newly produced virus infectious.

In accordance with one aspect of the invention, the cleavage of Influenza hemagglutinin by a protease is physically separated from the primary cultivation of the host cells and the infection of the host cells by the virus. This allows much higher protease concentrations than described in the prior art. In the prior art where the protease was part of the medium in the primary culture, protease concentrations had to be kept low to minimize the toxic effects on cellular processes and host cell growth rates. As a result, the activation of Influenza virus by proteolytic cleavage of hemagglutinin was not complete and non-infectious virus particles were maintained in the culture. Prior art approaches to deal with this problem involve growing Influenza virus in embryonated chicken eggs. This technique, however, has many disadvantages as there are many labor intense steps which are susceptible to contamination.

According to the invention, following incubation of host cells with virus for a time span allowing at least one round of virus replication, one or more proteases are added. According to one aspect of the invention, protease activation of virus occurs in a location removed from the primary culture vessel, by employing an "activation vessel" which can be a column, pipe, tube, coil, or other container which facilitates contacting the virus with the activating protease, while eliminating or minimizing the cell toxic effects of the protease. Accordingly, a new and inventive method is provided that allows the use of proteases, such as subtilisin A, at much higher concentrations than those normally tolerated by culture cells to thereby further increase the level of viral activation, such as Influenza HA cleavage.

Following incubation of medium containing infected cells, virus and one or more proteases in the activation vessel of the loop, the proteases are inactivated or removed by protease inhibitors or the like. According to one aspect of the invention, this neutralization step occurs in a location which is separate from both the primary culture vessel and the activation vessel.

After efficient inactivation of the proteases, the activated viruses can be recycled back into the cultivation process without a negative interference of the proteases with the growth of the host cells. Because of these aspects, the present invention provides an advantageous and efficient method for the continuous production and harvesting of viruses The augmentation loop aspect of the present invention is adaptable to the production of any type of virus and any type of cellular product. The augmentation loop system of the present invention allows the independent optimization of parameters of cell growth and synthesis rates. Therefore, the augmentation loop system can be used in all cases where efficient synthesis rates of a virus or another cellular product, for example, a recombinant protein, require an activation step that otherwise would be toxic or harmful to cellular processes of the primary culture.

Due to the physical separation of fermentation, activation, and inactivation steps, the activation and inactivation steps can occur under chemical or physical conditions that otherwise would not be tolerate by cells in a conventional cell culture system. As a consequence, the activation steps of the present invention are more efficient and highly increase production rates. Conditions that are not tolerated by cells in a conventional cell culture system can be of chemical or physical nature, that is, substances that are required at concentration that are harmful to cells as well as physical conditions such as temperatures or pressures that are harmful to cells when exhibited for a certain time span.

The Influenza viruses produced at high yields according to the present invention may be of diverse origin. They may be wild-type Influenza viruses that are directly isolated from throat swabs of infected mammals, preferably humans. For example, according to one aspect of the present method, a throat swab from a human infected with any strain of Influenza virus is diluted and used to inoculate directly the protein-free vertebrate cells provided by the present invention.

The Influenza viruses that can be produced at high yield according to the present invention may further be wild-type Influenza viruses that have been previously passaged through host cells prior to inoculation of the protein-free vertebrate cells. The passaging may have occurred either in embryonated chicken eggs or in vertebrate culture cells, for example VERO, MDCK, MDBK, LLC-MK2 or CV-1 cells, in primary chicken embryo cell lines or in cell aggregates that comprise a plurality of cell types, for example, from vertebrate embryos.

The Influenza viruses may still further be reassortant Influenza viruses or donor Influenza viruses, such as viruses with high yield or attenuated virulence phenotypes. According to the present invention, attenuated virulence viruses include temperature-sensitive or cold-adapted Influenza virus strains.

In one specific embodiment according to the present invention, the protein-free vertebrate culture cells are VERO cells. VERO cells are advantageous in that they are among the few cell lines that are registered for the production of vaccines to be used in human medicine. Thus, additional approval for use of VERO cells to produce vaccines to be used to immunize humans is unnecessary. Until the present invention, however, attempts to use VERO cells for the production of Influenza virus have resulted in unacceptably low yields, or required the use of protein-containing mediums and multiple passaging.

In one embodiment of the present invention, the virus that is propagated to finally produce a virus vaccine, is a reassortant orthomyxovirus, preferably an Influenza virus. Reassortment is a specific feature of segmented viruses, for example Influenza viruses. Double infection of a host cell, that is, infection of the host cell with at least two strains of segmented viruses such as Influenza virus, leads to the production of a mixture of segments derived from the two infecting viruses in one single host cell. During virus assembly, theoretically all combinations of these segments are possible.

Therefore, some of the virus progeny are identical to one of the originally infecting viruses, and other progeny are new combinations, that is, "reassortants." Desired reassortants can be specifically selected for the preferred activities by suppressing or eliminating viruses with undesired properties. Suppression or elimination can be accomplished with the appropriate antibodies directed against the undesired antigens.

There are prior art methods for obtaining reassortants. See Kilbourne, E. D. in Plotkin S. A., and Mortimer, E. A. eds., *Vaccines,* 1994. Briefly, a donor Influenza virus and an Influenza virus strain for which a vaccine is to be made are used to simultaneously infect the chick embryo allantoic sac. The technique, as it is described in the prior art, employs donor viruses that have been passaged in eggs for several times. Importantly, according to the prior art, the process leading to reassortment occurs in the egg. This has the disadvantage of selecting for egg-specific virus variants. Egg-specific virus variants do not necessarily fully represent the antigenicity of the Influenza variants that spread in the population from human to human. Accordingly, the efficiency of immunity of vaccines developed with reassortant viruses which were selected for egg-specific virus variants may be reduced.

The problems associated with the prior art can be avoided according to the present invention. According to the invention, a donor virus is a virus that preferably provides properties to the reassortant other than outer surface antigenicity. Donor properties may be those relating to a high-yield phenotype, an attenuated virulence phenotype or other desired phenotypes. Accordingly, a donor virus provides desired properties to the reassortant virus without adversely interfering with ability of the reassortant virus to simulate or mimic the outer antigenic properties of the influenza virus for which a vaccine is desired.

With antibodies suppressive to the outer surface antigens of the donor virus, reassortants are selected wherein the antigenic properties of the desired virus are coupled to the desired properties of the donor virus. For example, a "high yield donor Influenza virus" is one of the viruses preferably employed to produce a reassortant Influenza virus. The present invention provides a method for the production of such a high yield donor Influenza virus. Specifically, a culture of vertebrate cells is provided, preferably mammalian cells, for example VERO, CV-1, LLC-MK2, MDCK or MDBK cells, wherein the cell culture has been adapted to protein-free growth conditions for at least one generation, preferably for at least six cell generations, more preferably for at least twelve cell generations, even more preferably for at least eighteen cell generations and still more preferably for at least twenty-four cell generations before infection with a virus. This culture is infected with wild-type Influenza virus.

The wild-type Influenza virus may be directly isolated from a mammal infected with Influenza virus, preferably a human. The present invention provides for the direct isolation of a wild-type Influenza virus by means of methods comprising, for example, the steps of taking and diluting a throat swab from the infected mammal, and infecting directly a protein-free culture of vertebrate cells. The wild-type Influenza virus may further be passaged in embryonated chicken eggs or mammalian culture cells, for example in VERO cells, MDCK cells or in cell aggregates that comprise a plurality of cell types, for example from vertebrate embryos prior to propagation in a culture of protein-free vertebrate cells according to the present invention.

Regardless of its origin, the wild-type virus is then incubated with the culture of vertebrate cells. The cells can be selected for the best growing Influenza virus strain. This best growing Influenza strain is isolated and purified according to methods known in the art and becomes the parent strain or "high yield Influenza donor virus" for all types of reassortant Influenza viruses as they are provided by additional aspects according to the present invention.

A salient aspect of the present invention is that the high yield donor Influenza virus is well-adapted for high yield amplification in vertebrate culture cells. In one specific embodiment of the present invention, the high yield donor Influenza virus is perfectly adapted for high yield amplification in VERO cells.

In one particular embodiment, for example, the present invention provides a high yield donor Influenza virus which is both perfectly adapted to vertebrate cells and which has never had any contact with egg material. For instance, as Example 11 shows, one high yield donor Influenza virus strain is A/Orth/17/95 (H1N1). A/Orth/17/95 (H1N1) is a high yield donor Influenza virus that was directly passaged from a throat swab of a human patient infected with an Influenza virus strain of the 1994/1995 season onto VERO cells growing in a protein-free medium. It is perfectly adapted to VERO host cells and gives high yield output of virus and virus antigens in VERO cells. Significantly, strain A/Orth/17/95 (H1N1) has never had contact with chicken egg material, that is, the strain is 100% free of egg material. A further advantage of strains according to the invention pertains to the fact that they have been selected for high yield amplification in a mammalian cell line and not for egg-specific or egg embryo-specific adaptability.

In order to raise antibodies that bind to the outer surface antigens of the high yield donor Influenza virus, the present invention further provides a method that comprises isolating the outer surface antigens of the high yield donor Influenza virus and the administration of the isolated antigens to a mammal. The isolation of the outer surface antigens of Influenza virus employs cleavage of the antigens off the virus envelope by bromelin. According to the present invention, the outer surface antigens are the glycoproteins hemagglutinin and neuraminidase of a high yield donor Influenza virus.

The present invention still further provides the antibodies that bind to outer surface glycoproteins of a high yield donor Influenza virus. In one specific embodiment, the antibodies bind to the outer surface glycoproteins, hemagglutinin and neuraminidase of the high yield donor Influenza virus A/Orth/17/95 (H1N1). One specific aspect of the present invention is the production of reassortant Orthomyxoviruses, preferably influenza viruses.

One approach of producing reassortants according to the present invention is as follows: First, a culture of vertebrate cells is provided, preferably mammalian cells, for example VERO, CV-1, LLC-MK2, MDCK or MDBK cells, that have been adapted to protein-free growth conditions for at least one generation, preferably for at least six cell generations, more preferably for at least twelve cell generations, even more preferably for at least eighteen cell generations and still more preferably for at least twenty-four cell generations before infection with a virus. This culture is co-infected with two different Influenza virus strains, Influenza virus strains (I) and (II).

For the purposes of explanation, Influenza virus strain (II) is an Influenza virus strain designated for vaccine production. The outer surface glycoproteins of virus strain (II) are the antigens that are desired to be contained in a vaccine. Typically, Influenza virus strain (II) may variy from season to season. The WHO determines which Influenza strain is designated for vaccine production for each season. Since the designated vaccine must present the outer surface antigens of a virus causing a current Influenza epidemic, this virus cannot be chosen freely by the manufacturer of a vaccine.

Typically, a wild-type Influenza virus strain resists high yield production. Often, a manufacturer prefers to employ viruses with attenuated virulence for use as live viral vaccine. Accordingly, a donor influenza virus that exhibits attenuated virulence, as an alternative or in addition to high-yield, can be employed to make the reassortant virus.

Accordingly, the present invention provides an approach for obtaining viruses with the capability of high yield and/or attenuated virulence while possessing the desired antigenicities of the virus against which the vaccine is to be developed. The inventive approach yields reassortant viruses that are free of undesired antigenicities and contaminants that otherwise would rise from production in eggs or chicken embryos.

For the production of Influenza virus reassortants, a protein-free culture of vertebrate cells according to the present invention is provided. After co-infection of this cell culture with Influenza virus strains (I) and (II), the culture is incubated to propagate each of the two different Influenza virus strains and all types of reassortants of these viruses. A desired reassortant Influenza virus strain is then selected. For the selection of the desired reassortant Influenza virus strain, specific selection antibodies are employed. See Kilbourne E. D. in Plotkin S. A. and Mortimer E. A. eds. *Vaccines*, (1994).

The specific selection antibodies are directed to the outer surface glycoproteins of the donor virus, typically, hemagglutinin and neuraminidase. The specific selection antibodies are incorporated into the medium for several growth cycles. By binding to the outer surface glycoproteins of the donor virus, be it on an identical descendant of the original donor virus or on a reassortant that carries hemagglutinin and/or neuraminidase of the donor virus, these antibodies suppress amplification of the unwanted virus strains. Only viruses that carry the outer surface antigens of the Influenza virus designated for vaccine production can therefore proliferate. Upon several growth cycles, which include the suppressing antibodies, the desired reassortants are strongly enriched and can be isolated. The isolated reassortant can then be propagated according to the present invention and vaccines will be prepared from the reassortant.

In one embodiment of the invention, Influenza virus strain (I) that is used to produce a reassortant Influenza virus is a high yield donor Influenza virus. The method for the production of such a high yield donor as well as the high yield donor Influenza virus itself are provided by the present invention. The high yield phenotype of the reassortant is selected by multiple passaging. The selected reassortant carries the gene segments encoding the outer surface glycoproteins provided by virus strain (II) and all the gene segments responsible for the high yield phenotype of virus strain (I). Segments that have not been under selective pressure may be from any of the two virus strains.

In another embodiment, Influenza virus strain (I) that is used to produce a reassortant Influenza virus is an Influenza virus with attenuated virulence. The production of attenuated virulence Influenza virus is known in the art. For the production of a reassortant virus carrying the outer surface antigens of an Influenza virus strain designated for vaccine production and the attenuated phenotype of a donor Influenza virus, an "attenuated master strain" is desirable. An attenuated master strain is one that has been tested and shown to be attenuated in humans and can pass this attenuated characteristics to reassortants through the donation of gene segments other than those encoding the outer surface glycoproteins. Attenuated master strains that can be used as Influenza virus strains (I) are preferably cold-adapted or temperature-sensitive virus mutants.

The selected reassortant carries the gene segments encoding the outer surface glycoproteins provided by virus strain (II) and the gene segments containing the determinants of the attenuated phenotype of virus strain (I). Segments that are not associated with any of these features can be derived from virus strain (I) or virus strain (II).

Reassortant Influenza viruses that carry the outer surface antigens of an Influenza virus strain designated for vaccine production and the attenuated phenotype of a donor Influenza virus can be used to produce a live Influenza virus vaccine, that is, vaccine viruses that do not have to be inactivated prior to administration to a human or other mammal.

The present invention provides a reassortant Influenza virus, that carries the outer surface antigens of an Influenza virus designated for vaccine production and exhibits a high yield or an attenuated phenotype derived from the appropriate donor virus strain. All reassortant viruses can be propagated by the method of the present invention.

In one specific embodiment of a reassortant virus according to the present invention, the virus is an Influenza virus carrying the hemagglutinin and the neuraminidase of a virus designated for vaccine production and the high yield phenotype of a high yield donor virus. For example, a specific embodiment of this aspect of the invention is achieved when the high yield donor virus is A/Orth/17/95 (H1N1).

In another embodiment of the invention, the reassortant virus is an Influenza virus carrying both the hemagglutinin and the neuraminidase of a virus designated for vaccine production as well as the attenuated phenotype of an attenuated master virus strain. In one more specific embodiment of this aspect, the attenuated master virus strain is a temperature-sensitive mutant Influenza virus strain. In yet another more specific embodiment of this aspect, the attenuated master virus strain is a cold-adapted Influenza virus strain. The reassortant Influenza viruses of this aspect can be used to produce live virus vaccine.

In another preferred embodiment, a virus that is directly derived from an infected human or other mammal, is grown in a culture of vertebrate cells according to the present invention, that is, a culture that has been pre-adapted to protein-free growth conditions. In an additional specific embodiment, the virus that is directly derived from an infected mammal, preferably a human, is an Influenza virus that is directly taken from the infected mammal and contacted with a culture of vertebrate cells according to the present invention, that is, a culture that has been pre-adapted to protein-free growth conditions.

If an Influenza type virus is derived from a recently infected mammal, such a virus is likely to be the cause of a current epidemic and thus will be a virus strain that is designated for vaccine production.

It has been described that chicken eggs select subpopulations of Influenza virus are antigenically distinct from virus from the same source grown in mammalian cell cultures (Schild et al., 1983. Nature 303:706–709). Employing mammalian cell cultures, the production of an Influenza virus strain derived from a recently infected mammal according to the method described in the present invention leads to a homogeneous Influenza virus progeny that displays identical or highly similar antigenic properties as the Influenza virus that is directly taken from the infected mammal. Thus, the present invention provides a method that eliminates the selection of host cell variants while still providing for the retention of the original antigenic properties of the virus, even after multiple passaging.

During the production process, it may be desirable to adapt the subject virus to a specific host cell. Adaptation can be accomplished by altering the cleavability of the hemagglutinin (HA) of the adapted virus. Alterations in the cleavability of the HA of a particular virus strain can be generated by known site-directed mutagenesis and PCR techniques. By employing these techniques in the present invention, virtually any Influenza virus strain can be modified to be susceptible to enzyme activation. This can be done while maintaining the native immune profile of the hemagglutinin. Thus, the methodology of the present invention allows the large scale production of all types of Influenza virus to a high titre.

In accordance with one aspect of the invention, the Influenza virus is modified to create a modified, and preferably more efficient, cleavage site in the hemagglutinin. Such a modulated cleavage site is preferably KKRKKR or the like, that is, lysine, lysine, arginine, lysine, lysine, arginine, which are basic amino acids. The modulated cleavage site is designed according to the invention to replace the naturally occurring hemagglutinin cleavage size of any type of Influenza virus. The preferred (or "master") cleavage site KKRKKR, was designed according to the consensus sequence for protease recognition, R-X-K/R-R as described by Vey et al., *Virology,* 188: 408–13 (1992).

Thus, the present invention comprises the advantageous aspect of altering the susceptibility of a virus strain to a protease, such as trypsin, in the event that a strain should arise which cannot be activated by other methodologies. In the case of Influenza, there are several structural properties of the HA that determine the differential cleavability, but the key factor is the amino acid sequence at the cleavage site. It has been demonstrated that susceptibility of hemagglutinin to cleavage is not a fixed characteristic of the molecule. The present invention provides advantageously for the alteration of hemagglutinin to ensure its susceptibility to cleavage by available proteases.

Specifically, hemagglutinin can be altered to adapt subject virus to a novel host cell. Cleavability of the hemagglutinin of the adapted virus in a new host cell type can sometimes be obtained by a single amino acid substitution close to the cleavage site. Thus, alterations in the cleavability of the HA of a particular virus strain can be generated by known site-directed mutagenesis and PCR techniques. By employing these techniques in the present invention, virtually any Influenza virus strain can be modified to be susceptible to enzyme activation. This can be done while maintaining the native immune profile of the hemagglutinin. Thus, the methodology of the present invention allows the large scale production of all types of Influenza virus to a high titre.

Until the present invention, it was only possible to grow high yields of Influenza virus when the virus strains themselves provided an efficient cleavage site. The modification of the hemagglutinin cleavage site as it is provided by the present invention enables the growth in vertebrate cell culture of any type of Influenza virus to high yield. As a consequence, vaccines can be prepared that are effective against all Influenza strains present in a given population at a certain time.

According to one aspect of the invention, high yield production of Influenza virus is accomplished by an increase in the level of HA-activation, that is, activation of the virus, and the use of an augmentation loop system, whereby virus containing medium from a cell fermentor containing cells cultured and infected according to the present invention is continually removed to a vessel containing one or more proteases, such as trypsin. After a certain incubation time, the medium is transferred to a vessel containing a substance which inhibits or removes the protease activity, and, finally, the medium is subsequently returned to the cell containing fermentor.

In one embodiment, the present invention provides a method of producing Influenza virus that is characterized by highly advantageous features. The present method, inter alia, allows the high yield production of Influenza virus, allows the use of concentrations of proteases much higher than in previous methods, and, consequently, the efficient activation of viruses, including all strains of Influenza virus. Moreover, due to the flexibility of the present method, its augmentation loop aspect allows the ready adaptation of production conditions to any serotype of Influenza and other viruses.

An additional advantage is found in the aspects that relate to the modification of the cleavage site of a protein involved in activation, such as Influenza hemagglutinin, to thereby permit substantial increases in the yield of viruses that with conventional methods can be cultivated at low yield only. Further advantages of the presently claimed method relate to its resultant production of Influenza virus which is substantially free of egg proteins. In addition, the present method for Influenza virus production gives a much higher virus titre when compared with other cell culture methods. Also, the present invention provides a method which enables the growth of all human Influenza virus strains tested to levels approaching that obtained in the embryonated egg without the disadvantages of using the embryonated egg. Finally, the method allows upscaling of the virus production to large-scale fermentors, thereby permitting the attainment of high production efficiencies.

The advantages of the present invention are illustrated in the following examples. The examples are illustrative of the invention but do not limit its scope. In the examples and tables below, B/Massachusetts refers to B/Massachusetts/71; B/Panama refers to B/Panama/45/90; B/Yamagata refers to B/Yamagata/16/88; Brazil refers to A/Brazil/11/78

(H1N1); California refers to A/California/10/78 (H1N1); Singapore 6 refers to A/Singapore/6/86 (H1N1); Taiwan refers to A/Taiwan/1/86 (H1N1); Texas 36 refers to A/Texas/36/91 (H1N1); USSR refers to A/USSR/90/77 (H1N1); A2 Singapore refers to A/Singapore/1/57 (H2N2); Beijing refers to A/Beijing/353/89 (H3N2); Guizho refers to A/Guizho/54/89 (H3N2); Hongkong refers to A/Hongkong/1/68 (H3N2); Hongkong 5 refers to A/Hongkong/5/83 (H3N2); Shanghai 16 refers to A/Shanghai/16/89 (H3N2); Texas refers to A/Texas/1/77 (H3N2); and Victoria refers to A/Victoria/3/75 (H3N2).

EXAMPLE 1

Hemagglutinin Titre, Obtained from Various Influenza Strains Produced by Embryonated Eggs and Spinner Culture with or without Proteases Influenza strains listed in Table 1 were used either for infection of embryonated chicken eggs or the CEC spinner culture.

The CEC-spinner culture aggregates were produced by mechanically disintegrating embryos isolated from chicken eggs as disclosed in WO 91/09937. Two embryonated eggs are required to generate 100 ml of biomass culture. 100 ml CEC spinner culture were infected with 1 ml of Influenza virus containing allantoic fluid. Addition of the protease was immediately carried out after infection. Either Trypsin (Seromed) or Subtilisin A (Fa. Novo) were added to the medium to a concentration of 20 mU/ml and 30 μg/ml, respectively. The CEC spinner culture was incubated for 3–4 days with removal of the half of the medium volume (50 ml) every day. Fresh medium with or without protease was added to an end volume of 100 ml culture. After 4 days of incubation and daily harvesting of virus-containing medium, the pooled cell culture medium was collected and the HA-titre was determined. The HA-titre was determined as described by Hirst, "The Agglutination of Red Cells by Allantoic Fluid of Chick Embryos Infected with Influenza Virus", Science, 94:22–23 (1941) and Barrett et al., "Viruses" in Methods of Immunological Analysis, Masseyeff R. F., Albert W. H., and Staines N. A. (eds), Vol. 2, VCH Weinheim, 116–132 (1993).

10–11 day old embryonated eggs were infected with 200 μl virus containing allantoic fluid per egg. Infected eggs were incubated for 2–3 days at 37° C. as described by Burnett, "Influenza Virus Infections of the Chick Embryo by the Amniotic Route", Austral. J. Exp. Biol. Med. Sci., 18: 353–360 (1940). The egg was opened and the HA titre was determined as already described.

Table 1 compares the hemagglutinin titre obtained from various Influenza strains produced by embryonated eggs and spinner culture with or without proteases. The data show that the use of the CEC spinner culture and the addition of protease according to the present invention increases the yield of the most strains to a level approaching the yields of virus strains grown in the embryonated egg cultures, all without the disadvantages inherent in other culture methods.

TABLE 1

Maximum HA-Titre obtained for different Influenza strains in embryonated eggs and in CEC-spinner-cultures with and without the proteases Trypsin and Subtilisin A

| | | | HA-Titre | | | |
|---|---|---|---|---|---|---|
| | | Vaccine | CEC spinner culture/Protease | | | |
| Subtype | Strain | Year | none | Trypsin | Subtilisin A | Egg |
| B | B/Massachusetts | | 7 | 8 | n.d. | 9 |
| | B/Panama | 1991/92, 92/93 | 6 | 4 | 5 | 8 |
| | B/Yamagata | 90/91, 91/92, 92/93 | 3 | 5 | 5 | 8 |
| A/H1N1 | Brazil | | 7 | 1 | n.d. | 10 |
| | California | | 2 | 2 | 6 | 8 |
| | USSR | | 7 | 2 | n.d. | 10 |
| | Singapore 6 | 190/91, 91/92, 92/93 | 2 | 4 | 4 | 7 |
| | Taiwan | 1991/92 | 4 | 6 | 4 | 9 |
| | Texas 36 | 1992/93 | 5 | 4 | n.d. | 6 |
| A/H2N2 | A2 Singapore | | 2 | 7 | n.d. | 9 |
| A/H3N2 | Hong Kong | | 2 | 8 | 6 | 10 |
| | Hong Kong 5 | | 2 | 7 | 6 | 8 |
| | Texas | | 2 | 6 | n.d. | 8 |
| | Victoria | | 2 | 6 | n.d. | 8 |
| | Guizho | 1990/91 | 2 | 6 | 5 | 6 |
| | Shanghai 16 | 1990/91 | 2 | 6 | 6 | 6 |
| | Beijing | 1991/92, 92/93 | 2 | 6 | 6 | 8 | n.d. = not done

EXAMPLE 2

Virus Yield Obtained from Various Influenza Strains Produced by Embryonated Eggs and CEC Biomass Culture Embryonated eggs and biomass CEC spinner culture were infected with various strains of Influenza virus as listed in Table 2 and described in Example 1.

The embryonated egg yields a maximum of 7 ml allantoic fluid, which is harvested 72 hours after inoculation. Two embryonated eggs are required to produce 100 ml of biomass culture. By harvesting half of the culture volume after 48 and 72 hours and the total volume after 96 hours, 200 ml of virus containing medium were collected over a 96 hour period. The biomass culture provided 100 ml virus antigen per egg compared to a maximum of 7 ml from the inoculated egg, which is a 14-fold increase in volume. When this factor is taken into account, the present method produces a higher virus antigen yield when compared with the embryonated egg method. This is illustrated by the calculations in Table 2.

Table 2 compares the virus yield obtained from various Influenza strains produced by embryonated eggs and by those produced by the present invention. The HA-titre was calculated as already described for 100 ml of biomass spinner culture medium obtained from one egg and 7 ml of allantoic fluid per egg. Thus, the data in Table 2 present the total virus yield per egg in CEC spinner culture obtained with or without proteases, calculated from the results of Example 1. Dependent on the Influenza strain used, the biomass spinner culture method results in an approximately 2–14 fold increase in virus antigen compared to the yield obtained in the embryonated egg. Incubation of the infected biomass spinner culture without the addition of a protease reached a virus yield close to that obtained in eggs for B-Panama, Brazil, USSR and Texas 36, which could not be increased by the protease. The virus yield of all other Influenza virus strains was increased by the addition of a protease. Thus, insufficient endogenous protease content of the biomass cell culture can be overcome by the exogenous addition of a protease to activate the viral hemagglutinin.

TABLE 2

Comparison of Virus Yield in Embryonated Egg and Biomass Culture Total Yield/Egg

| | | Biomass Culture | | Egg | Ratio Biomass |
|---|---|---|---|---|---|
| Subtype | Strain | Protease | HA Units × 100 ml | HA Units × 7 ml | Culture/Egg |
| B | B/Mass. | T | 25600 | 3584 | 7.1 |
| | B/Panama | N | 6400 | 1792 | 3.6 |
| | B/Yamagata | T | 3200 | 1792 | 1.8 |
| A/H1N1 | Brazil | N | 12800 | 7168 | 1.8 |
| | California | S | 6400 | 1792 | 3.6 |
| | USSR | N | 12800 | 7168 | 1.8 |
| | Singapore 6 | T | 1600 | 896 | 1.8 |
| | Taiwan | T | 6400 | 3584 | 1.8 |
| | Texas 36 | N | 3200 | 448 | 7.1 |
| A/H2N2 | A2 Singapore | T | 12800 | 3584 | 3.6 |
| A/H3N2 | Hong Kong | T | 25600 | 7168 | 3.6 |
| | Hong Kong 5 | T | 12800 | 1792 | 7.1 |
| | Texas | T | 6400 | 1792 | 3.6 |
| | Victoria | T | 6400 | 1792 | 3.6 |
| | Guizho | T | 6400 | 448 | 14.3 |
| | Shanghai 16 | T | 6400 | 448 | 14.3 |
| | Beijing | T | 6400 | 1792 | 3.6 |

N: none
T: Trypsin
S: Subtilisin A

EXAMPLE 3

Large Scale-up of Influenza Virus Production in CEC Fermentor Cultures

A scale-up of the 100 ml spinner culture to an automated 2 liter fermentor was performed. A 2 liter fermentor of biomass cell culture was inoculated with 2 ml Influenza virus containing allantoic fluid with an HA titre of 6–8 with continuous medium changes at 37° C.

The method of the invention using large scale fermentor culture employs trypsin activation in an augmentation loop system, whereby portions of the medium containing the desired virus are continuously removed from the fermentor to a vessel containing trypsin or any other required protease. In the vessel containing trypsin or subtilisin A with a concentration of 20 mU/ml and 30 μg/ml, respectively, the virus is activated over a period of approximately one hour. The medium containing the trypsin activated virus is then pumped into a vessel containing soya bean trypsin inhibitor (Sigma) for about 1 h with a concentration sufficient to neutralize the residual trypsin activity. The medium containing neutralized trypsin with virus is then returned to the fermentor for a further cycle of replication. By continuous removal of the biomass cell culture medium from the fermentor and addition of fresh culture medium, 4–5 liters of virus-containing medium was obtained during a time period of 96 hours. The method of the invention allows activation of virus with much higher concentration of trypsin than would be possible with conventional methods, where high concentrations of the protease would have detrimental effects on the cell culture and virus if incubated with them over a prolonged period.

Table 3 shows the advantages of the method as applied to the virus strain California, which can be activated by trypsin using the augmentation loop system and later employing a trypsin inhibitor.

TABLE 3

Maximum HA-Titre obtained for different Influenza strains in 100 ml CEC-spinner cultures and 2 liter CEC-fermentor cultures

| | | | HA-Titre | | | |
|---|---|---|---|---|---|---|
| | | | CEC culture | | | |
| Subtype | Strain | Vaccine Year | Protease | spinner | fermentor | Egg |
| B | B/Panama | 91/92, 92/93 | N | 6 | 6 | 8 |
| A/H1N1 | Brazil | | N | 7 | 7 | 10 |
| | California | | S | 6 | 6 | 8 |
| | | | T | 2 | 6 | |
| | Singapore 6 | 90/91, 91/92, 92/93 | S | 4 | 4 | 7 |
| | | | T | 4 | 4 | |
| A/H3N2 | Hongkong 5 | | S | 6 | 6 | 8 |
| | | | T | 7 | 7 | |
| | Beijing | 91/92, 92/93 | S | 6 | 7 | 8 |
| | | | T | 6 | 7 | |

N: none
S: Subtilisin A
T: Trypsin

EXAMPLE 4

Comparison of HA Titre of Influenza Virus in MDCK Cell Culture, Standard CEC Culture and CEC Biomass Aggregates Embryonated eggs, CEC fermenter culture, CEC and MDCK monolayer cultures were infected with Influenza virus strains as Listed in Table 4. Infection of embryonated eggs were performed as described in Example 1 and with the fermentor culture as described in Example 3.

Primary chicken embryo cells were propagated as described by Mayr et al., *Arch. ges. Virusforsch.*, 10: 72–102 (1961) and infected with Influenza virus containing allantoic fluid with a HA titre of 6–8 units.

Continuous cell lines of MDCK cells were propagated as monolayers and infected with Influenza virus containing allantoic fluid with a HA titre of 6–8 units.

Incubation was carried out until development of maximum cytopathic effect (cpe) or for a maximum of 72 h and HA-titre was determined as previously described.

These data demonstrate that the method of invention produces higher yields for all viruses studied in the CEC fermentor culture than in CEC monolayer culture or other cell culture methods. Table 4 compares the HA titre obtained for different strains of Influenza A and a B strain in MDCK cell culture, standard CEC culture and CEC biomass aggregates in the presence and absence of trypsin and subtilisin A. Slightly higher titres can be obtained in MDCK cultures, but these cells are not licensed for human vaccine production. Activation of California, Singapore 6, Hongkong, Hongkong 5 and Beijing by trypsin or subtilisin leads to titres higher than those obtained with or without activation in standard CEC cultures or in MDCK culture.

TABLE 4

Comparison of HA titres of Various Influenza Strains in CEC Biomass Cultures, CEC Monolayer Cultures and MDCK Monolayer Cultures with and without addition of Proteases with titres in embryonated eggs

| | | | HA-Titre | | | | | | | |
|---|---|---|---|---|---|---|---|---|---|---|
| | | | | | | Tissue culture "monolayer"/Protease | | | | |
| | | Vaccine | CEC fermentor — culture | | | CEC | | MDCK | | |
| Subtype | Strain | Year | None | Trypsin | Subtilisin A | None | Trypsin | None | Trypsin | Egg |
| B | B/Panama | 91/91; 92/93 | 6 | 4 | 5 | 2 | 2 | 7 | 7 | 8 |
| A/H1N1 | Brazil | | 7 | 1 | n.d. | 5 | 5 | 8 | 8 | 10 |
| | California | | 2 | 6 | 6 | 2 | 2 | 5 | 5 | 8 |
| | Singapore 6 | 90/91; 91/92; 92/93 | 2 | 4 | 4 | 0 | 0 | 3 | 2 | 7 |
| A/H3N2 | Hongkong | | 2 | 8 | 6 | 2 | 5 | 6 | 6 | 10 |
| | Hongkong 5 | | 2 | 7 | 6 | 0 | 0 | 4 | 5 | 8 |
| | Beijing | 91/92; 92/93 | 2 | 7 | 7 | 2 | 2 | 5 | 6 | 8 | n.d. = not done

EXAMPLE 5
Antibody Response After Immunization with Influenza Virus Vaccine

The Influenza A H1N1 strain Brazil was grown in embryonated eggs as previously described and the allantoic fluids were harvested, pooled and frozen at −20° C. The same strain was also grown in CEC biomass fermentor culture as described previously. The tissue culture medium supernatant was concentrated by ultrafiltration using a 100,000 M.W. cut-off filter and this material and the allantoic fluid from embryonated cells were purified by ultracentrifugation over a 20% sucrose cushion. The virus pellets were resuspended in buffer and inactivated by U.V./psoralene treatment (10 μg/ml 4-aminoethyltrioxalen Hydrochloride, U.V. intensity of 20 mW/cm$^2$) for 15 minutes. The antigen preparations were then diluted to give a concentration of 20 μg/ml and adjuvanted with Al(OH)$_3$.

Groups of ten mice were then immunized with a dose of 10 μg antigen and boostered with the same dose four weeks later. Two weeks after the booster injection, the animals were sacrificed and serum HAI titre and ELISA titre was determined as shown in Table 5.

These data demonstrate that there was no significant difference in the HAI and ELISA antibody titres generated by immunization with the Brazil strain grown by standard egg technology or by the claimed method of this invention.

TABLE 5

Comparison of Antibody Response in Mice (Pool of 10 immunized mice each) After Immunization with Vaccines Produced in Embryonated Eggs and Mice Immunized with Vaccines Produced in a CEC Biomass Fermentor

| | | Embryonated Egg | | | Fermentor | | |
|---|---|---|---|---|---|---|---|
| | | Antibody Titre | | | | Antibody Titre | |
| Subtype | Strain | HAI | ELISA | Protease | HAI | ELISA | |
| A/H1N1 | Brazil | 2560 | 102400 | — | 2560 | 102400 | |
| | California | 2560 | 51200 | S | 5120 | 102400 | |
| A/H3N2 | Hong Kong 5 | 2560 | 204800 | T | 2560 | 102400 | |
| B | B/Panama | 160 | 102400 | — | 160 | 102400 | |

—: none
T: Trypsin
S: Subtilisin A

EXAMPLE 6
Comparison of HA Titres of Different Influenza Strains in VERO Monolayer Cultures in Conventional Medium Containing Fetal Calf Serum and in Protein-free Medium in the Presence and Absence of Trypsin Conventional VERO cells and protein-free VERO cells were infected with Influenza virus strains as listed in Table 6. Continuous cell lines of VERO cells were propagated as monolayers in either conventional DMEM medium (Dulbecco's Eagle Medium) containing 5% fetal calf serum (FCS) or in protein-free DMEM medium. Cells were infected with Influenza virus containing allantoic fluid with a HA titre of 6–8 units. Incubation was carried out until development of maximum cytopathic effect or for a maximum of 72 hours and HA titres were determined as described previously. After infection, the medium contained either no trypsin or 0.002% trypsin (Seromed). The data summarized in Table 6 demonstrate that the addition of trypsin to a medium containing 5% FCS for some virus strains allows low yield virus production.

Significantly, the use of protein-free medium plus trypsin, however, gives high yield production for all virus strains tested.

TABLE 6

Maximum HA-titres obtained for different
Influenza strains in conventional VERO monolayer
cultures and in protein-free VERO monolayer cultures
with and without trypsin

| | | Vaccine | Conventional VERO "monolayer" | | protein-free VERO "monolayer" | |
|---|---|---|---|---|---|---|
| Subtype | Strain | Year | −trypsin | +trypsin | −trypsin | +trypsin |
| A/H1N1 | Brazil | | 0 | 3 | 5 | 8 |
| | California | | 0 | 0 | 0 | 6 |
| A/H3N2 | Hongkong | | 0 | 3 | 0 | 6 |
| | Hongkong 5 | | 0 | 3 | 0 | 7 |
| | Beijing | 91/92; 92/93 | 0 | 0 | 2 | 8 |

EXAMPLE 7
Comparison of HA Titres Obtained for Different Influenza Strains in Embryonated Eggs, Protein-free VERO Monolayer Cultures and in Protein-free VERO Fermentor Cultures in the Presence and Absence of Trypsin Embryonated eggs, protein-free VERO monolayer cultures and protein-free VERO fermentor cultures were infected with Influenza virus strains as listed in Table 7. Infection of embryonated eggs was performed as described in Example 1 and of fermentor culture as described in Example 3. Continuous cell lines of protein-free VERO cells were propagated as monolayers and infected with Influenza virus containing allantoic fluid with a HA-titre of 6–8 units. Incubation was carried out until development of maximum cytopathic effect (cpe) or for a maximum of 72 hours and HA-titre was determined as previously described.

The data were summarized in Table 7 demonstrate that the different virus strains grown in protein-free VERO cells approach the HA-titres of the virus strains grown in embryonated eggs.

EXAMPLE 8
Comparison of HA Titres Obtained from Various Influenza Strains in CV-1 and LLC-MK 2 Cells Cultivated in the Presence of Serum or Under Protein-free Conditions CV-1 cells and LLC-MK 2 cells were grown as monolayers under protein-free conditions (PF) or under protein-containing conditions In the presence of 5% fetal calf serum (FCS) as indicated in the table. Cells were infected with Influenza virus containing allantoic fluid with a HA-titre of 6–8. Influenza virus strains were as indicated in the table. To demonstrate the effect, of trypsin on HA-titres, all experiments were performed in the absence of trypsin or in the presence of 0.002% trypsin as indicated in Table 8. Experiments were performed as described in Example 6.

The data summarized in Table 8 demonstrate that for both cell lines, CV-1 and LLC-MK, maximum HA-titres are obtained under protein-free conditions and in the presence of trypsin.

TABLE 8

Maximum HA-titers obtained for Influenza
strains in CV-1 and LLC-MK 2 cells cultivated in the
presence of serum (FCS) or under protein-free
conditions (PF)

| | | HA-Titre | | | | | |
|---|---|---|---|---|---|---|---|
| | | Brazil | | Beijing | | Hongkong 5 | |
| Cell-line | Protein | −trypsin | +trypsin | −trypsin | +trypsin | −trypsin | +trypsin |
| CV-1 | FCS | 3 | 5 | 2 | 3 | 0 | 0 |
| | PF | 6 | 7 | 7 | 7 | 5 | 8 |
| LLC-MK2 | FCS | 0 | 0 | 0 | 0 | 0 | 0 |
| | PF | 2 | 7 | 2 | 7 | 0 | 6 |

EXAMPLE 9
Comparison of HA Titres Obtained from Various Influenza Strains in MDCK Cells Cultivated in the Presence of Serum or Under Protein-free Conditions MDCK cells were grown as monolayers under protein-free conditions (PF) or under protein-containing conditions in the presence of 5% fetal calf serum (FCS) as indicated in Table 9. Cells were infected with Influenza virus containing allantoic fluid-with a HA-titre of 6–8. Influenza virus strains were as indicated in Table 9. To demonstrate the effect of trypsin on L-titres, all experiments were performed in the absence of trypsin or in the presence of 0.002% trypsin as

TABLE 7

Maximum HA-titres obtained for different
Influenza strains in embryonated eggs, in protein-free
VERO monolayer cultures and in protein-free VERO
fermentor cultures with and without trypsin

| | | | HA-Titre | | | | |
|---|---|---|---|---|---|---|---|
| | | Vaccine | −Trypsin | | +Trypsin | | |
| Subtype | Strain | Year | Monolayer | Fermentor | Monolayer | Fermentor | Egg |
| B | B/Panama | 91/92, 92/93 93/94, 94/95 | 6 | 0 | 8 | 7 | 8 |
| A/H1N1 | Brazil | | 5 | 0 | 8 | 8 | 10 |
| | Singapore 6 | 90/91, 91/92 92/93, 93/94 94/95 | 3 | 0 | 6 | 6 | 7 |
| | Taiwan | 91/92 | 5 | n.d. | 6 | n.d. | 9 |
| A/H3N2 | Hongkong 5 | | 0 | 0 | 7 | 7 | 8 |
| | Beijing | 91/92, 92/93 | 2 | 0 | 8 | 8 | 8 |
| | Shang 16 | 90/91 | 2 | n.d. | 8 | n.d. | 6 |
| | Guizho | 90/91 | 2 | n.d. | 6 | n.d. | 6 | indicated in Table 9. Experiments were performed as described in Example 6.

The data summarized in Table 9 demonstrate that, as in the case of CV-1 cells and LLC-MK 2 cells, maximum HA-titres are obtained under protein-free conditions and in the presence of trypsin.

TABLE 9

Maximum HA-titers obtained for Influenza strains in MDCK cells cultivated in the presence of serum (FCS) or under protein-free conditions (PF)

| | | HA-Titre | | | | | |
|---|---|---|---|---|---|---|---|
| | | Brazil | | Beijing | | Singapore 6 | |
| Cell-line | Prot. | −Trypsin | +Trypsin | −Trypsin | +Trypsin | −Trypsin | +Trypsin |
| MDCK | FCS | 6 | 6 | 5 | 6 | 6 | 6 |
| | PF | 7 | 8 | 8 | 8 | 7 | 8 |

EXAMPLE 10

Alteration of the HA Cleavage Site of Influenza A/Hongkong/1/68 Virus Strain to the 'Master Cleavage Site' KXRKKR Influenza A/Hongkong/1/68 was grown in embryonated chicken eggs, antibody-purified, lysed and viral RNA was prepared according to standard site-directed mutagenesis methodology (Enami et al. *Proc. Natl. Acad. Sci. USA,* 87: 3802–3805 (1990)). The viral RNA was subjected to reverse transcription and PCR employing primers complementary to the terminal non-coding, conserved regions of HA. Due to the conservation of this region, the 5'-primer (Sequence 1: 5'-ATGATGTCTAGAAGCAAAAGCAGGGGATAATTC-3') and the 3'-primer (Sequence 2: 5'-ATGATGCTGCAG-TTTAGTGAGGGTTAATAGTAGTAACAAGGGTGTTTT-3') can be used for a wide range of Influenza virus strains. For further cloning, the 5'-primer carried a XbaI restriction site and the 3'-primer carried a PstI restriction site, additionally, the 3'-primer carried the T3-promoter sequence. After trimming of the restriction sites with the appropriate restriction enzymes (XbaI and PstI), the HA cDNA was subcloned into the XbaI and PstI sites of the multiple-cloning region of pUC19 (New England BioLabs) to obtain the pUC19-HA vector. Site-directed mutagenesis was performed as described by Palese et al. (WO 91/03552).

To mutate the HA cleavage site of Influenza A/Hongkong/1/68 to the 'master cleavage site', the sequence of the 3'-primer employed was (Sequence 3: 5'-ATGATG AGGC-CTCTTTTTTTTCTCTTTTTCTCTGGTACATTCCGCA-3'), wherein the nucleotide sequence TCT TTT TTT TCT CTT TTT is the reverse complement sequence of the sequence AAA AAG AGA AAA AAA AGA-3' that encodes the desired amino acid sequence, KKRKKR which replaces the original cleavage site, KQTR. Upstream of this nucleotide sequence, the 3'-primer carried a StuI restriction site, which allowed its fusion to the 3'-portion of the HA cDNA. The 5'-primer, Sequence 1, was the same as the 5'-primer employed for cloning as described above, that is, it did not carry any mutations with regard to Influenza A/Hongkong/1/68 and at its 5'-terminus it carried a XbaI restriction site.

The PCR-product was isolated and trimmed with the appropriate restriction enzymes (XbaI and StuI). The pUC19-HA vector carrying the HA cDNA of Influenza A/Hongkong/1/68 was also digested with the restriction enzymes XbaI and StuI to remove the portion of pUC19-HA that corresponded to the PCR-product. Instead of this portion, the trimmed PCR-product was ligated into the plasmid. The StuI restriction site occurs naturally in the HA sequence of Influenza A/Hongkong/1/68. To verify successful mutagenesis, the PCR-product inserted into the pUC19-HA vector carrying the PCR-product was linearized by digestion with Ksp632I and transcribed from the T3-promoter to give a negative strand RNA representing the HA segment of Influenza A/Hongkong/1/68 having an altered HA cleavage site of the amino acid sequence KKRKKR. Employing the ribonucleoprotein (RNP) transfection system according to Luytjes et al., "Amplification, Expression, and Packaging of a Foreign Gene by Influenza Virus", *Cell,* 59: 1107–13 (1989), an Influenza A/Hongkong/1/68 carrying the KKRKKR HA cleavage site was amplified in MDCK cells. In contrast to the method of Palese et al., no selection system was required since selection automatically preferred the more efficient cleavage site. Moreover, because there was no difference between the two types of virus other than the HA cleavage site, the two viruses, the original and the mutated version, belonged to the same serotype. The presence of the master cleavage site in the modified Influenza virus strain Influenza A/Hongkong/1/68 was confirmed by nucleotide sequencing on an Applied Biosystems 373 DNA Sequencer.

These data demonstrate that there was no significant difference in the HAI and ELISA antibody titres generated by immunization with the Brazil strain grown by standard egg technology or by the claimed method of this invention.

EXAMPLE 11

Construction of the High Yield Donor Influenza Virus Strain A/Orth/17/95 (H1N1)

A throat swab was taken from a patient showing all symptoms of an acute Influenza infection. The throat swab was diluted in 2 ml PBS, pH 7.2 and shaked to remove nasal cell material. With various amounts of this solution, a continuous cell line of protein-free VERO cells that had been propagated as monolayers were infected. After 3 days, the virus was placed onto new protein-free monolayer VERO cells. This was repeated three times. Then, one single virus strain was found to be enriched. Its high yield phenotype was determined by hemagglutination assay and its antigenic properties were determined by hemagglutination inhibition assay.

This Influenza virus strain was termed Influenza A/Orth/17/95 (H1N1) and became a high yield donor strain to be used in the production of virus reassortants. It has been passaged extensively in the laboratory while maintaining its high yield phenotype.

Hemagglutinin and neuraminidase of Influenza A/Orth/17/95 where prepared by treatment of purified virus with bromelin and purified by sedimentation on sucrose gradients. Goat polyclonal antiserum as well as monoclonal antibodies directed to the two glycoproteins of Influenza A/Orth/17/95 then were produced.

EXAMPLE 12

Construction of a High Yield Reassortant Influenza Virus Employing Strain A/Orth/17/95 (H1N1) as a High Yield Donor Virus Protein-free monolayer VERO cells were co-infected with various dilutions of the high yield donor virus Influenza A/Orth/17/95 and of an Influenza virus as it was recommended for vaccine production by the WHO for the season 1995/1996, A/Johannesburg/33/94 (H3N2). The progeny with the highest HA titre was treated with polyclonal antibodies directed against the outer surface glycoproteins, hemagglutinin and neuraminidase of Influenza A/Orth/17/95. The virus progeny was then passaged at limited dilution. Passaging in the presence of said polyclonal antibodies was repeated for two more times. Then, passaging was done once without the antibodies. This fourth passage was analyzed to determine the antigenic determinants of the reassortant virus which were clearly different from those of Influenza A/Orth/17/95 but identical to those of Influenza virus A/Johannesburg/33/94 (H3N2). The presence of hemagglutinin (HA) and neuraminidase (NA) of A/Johannesburg/33/94 on the outer surface of the reassortant virus was determined by hemagglutination inhibition assay using polyclonal antiserum directed against HA and NA of this specific virus strain.

EXAMPLE 13

Production of Protein-free VERO Cells

From the Ampoule Obtained from the ATCC (ATCC CCL 81) an aliquot was taken and inoculated in protein-free medium. After 4 cycles of cells through the medium, a working cell bank was obtained that was stored for further use.

From the working cell bank, roller bottles were used to grow the protein-free VERO cells to a density of $2.5 \times 10^8$/bottle after 4 cycles. Cells from 16 such bottles were transferred to a 12 l fermenter. The passaging was performed using pronase (concentration of $0.1$ mg/$10^8$ cells) to detach the cells from their support.

The fermenter culture was passaged 3 times to obtain $4 \times 10^{12}$ cells. These cells were then infected with the respective virus.

Virus propagation is described in the following examples. After virus propagation, the microcarriers were removed using a sieve (mesh 200), cells and cell fragments were removed by centrifugation at 30,500 g. Virus was prepared by ultrafiltration (NMWI, 200k).

Cultivation of VERO cells in protein-free medium gives a higher cell density than cultivation of VERO cells in serum-containing medium. A 7-day fermentation in a 150 l fermenter under protein-free conditions gives $2.2 \times 10^9$ cells/l, whereas a comparable cultivation in a medium containing 2.5% FCS gives $1.8 \times 10^9$ cells/l. The numbers given here represent the mean values of five individual experiments, respectively.

EXAMPLE 14

Production of TBE-virus and Vaccinia Virus in Protein-free VERO Cells

Protein-free VERO cells or conventional VERO cells were propagated in 900 cm² roller bottles. The protein-free VERO cells were kept under protein-free conditions in the medium described in example 13, conventional VERO cells were grown in the same medium to which 2.5% FCS was added. At a cell density of $2.8-3 \times 10^8$ cells, the VERO cells were inoculated with TBE virus (0.05 pfu/cell) or various recombinant Vaccinia virus strains (0.1 TCID 50/cell). The recombinant Vaccinia viruses used were vgp160MN which carries the HIV gp160 gene (EP 561 034), vPTI(FII) which carries the human Factor II cDNA (EP 561 034), FIX#5 which carries the human Factor IX cDNA (EP 561 034) and VPE-5 which carries the HIV env gene under the control of a T7-promoter (Barrett et al., *Aids Res. Human Retrovir.* 5: 159 (1989)).

Propagation of TBEV was determined by ELISA, yields of the recombinant Vaccinia viruses were determined by measuring the TCID50/ml. The results, which are given in Table 10, show clearly that protein-free VERO cells can propagate TBEV and recombinant Vaccinia virus as well as conventional VERO cells grown in serum-containing medium. In the case of recombinant Vaccinia virus FIX#5, the yield was increased in protein-free VERO cells when compared to the conventional VERO cell cultures.

TABLE 10

Comparison of TBEV and recombinant Vaccinia virus yields propagated on protein-free VERO cells with the yields from conventional VERO cells

| Virus (Strain) | culturing conditions | yield |
| --- | --- | --- |
| TBE virus | protein free | 5.2 µg/ml TBEV antigen |
| TBE virus | +FCS | 5.3 µg/ml TBEV antigen |
| rec Vaccinia vgp 160/MN | protein-free | $3.2 \times 10^7 TCID_{50}$/ml |
| rec Vaccinia vgp 160/MN | +FCS | $4.0 \times 10^7 TCID_{50}$/ml |
| rec Vaccinia VPE-5 | protein-free | $1.3 \times 10^8 TCID_{50}$/ml |
| rec Vaccinia VPE-5 | +FCS | $1.4 \times 10^8 TCID_{50}$/ml |
| rec Vaccinia FIX#5 | protein-free | $2.0 \times 10^8 TCID_{50}$/ml |
| rec Vaccinia FIX#5 | +FCS | $1.3 \times 10^8 TCID_{50}$/ml |
| rec Vaccinia vPTI (FII) | protein-free | $6.3 \times 10^8 TCID_{50}$/ml |
| rec Vaccinia vPTI (FII) | +FCS | $5.3 \times 10^8 TCID_{50}$/ml |

EXAMPLE 15

Comparison of HA Titres Obtained from Various Influenza Virus Strains in Embryonated Eggs with the Respective Titres Obtained in Protein-free VERO Cells with the Prokaryotic Proteases Subtilisin A (30 µg/ml) and Pronase (0.1 mg/$10^8$ Cells)

Protein-free VERO cells were produced as described in example 13. Cells were infected with Influenza virus containing allantoic fluid with a HA-titre of 6–8. Incubation was carried out until development of maximum cytopathic effect or for a maximum of 72 hours and HA titres were determined as described previously. The data summarized in Table 11 demonstrate that Influenza virus yields obtained by propagation in protein-free VERO cells in the presence of a prokaryotic protease, Subtilisin A or pronase, reach those obtained in the embryonated egg.

TABLE 11

Maximum HA-Titre obtained for different Influenza virus strains in embryonated eggs and in protein-free VERO (VERO-PF) spinner cultures with the proteases Subtilisin A and pronase

| Subtype | Strain | Vaccine Year | HA - Titre | | |
|---|---|---|---|---|---|
| | | | Subtilisin A | Pronase | Egg |
| B | B/Panama | 91/92, 92/93 93/94, 94/95 | 7 | nd | 8 |
| A/H1N1 | Brazil | | 8 | nd | 10 |
| | Singapore 6 | 90/91, 91/92, 92/93, 93/94, 94/95 | 7 | nd | 7 |
| | Texas 36 | 92/93 | 6 | 6 | 6 |
| A/H3N2 | Hongkong 5 | | 7 | nd | 8 |
| | Beijing | 91/92, 92/93 | 8 | nd | 8 |

EXAMPLE 16

Comparison of *Herpes Simplex* Virus (HSV-1) Yields Obtained with Protein-free VERO Cells and with Conventional VERO Cell Culture Protein-free VERO cells or conventional VERO cells incubated in medium containing 5% FCS prior to infection and 1% FCS after infection were infected with HSV-1 at multiplicities of 0.1, 0.05 or 0.001 $TCID_{50}$ per cell. The medium supernatant from infected cells was harvested when the cultures displayed 90–100% cytopathic effect.

TABLE 12

Propagation of HSV-1 in protein-free VERO cells or in conventional VERO cells

| Virus (MOI) HSV-1 | culturing conditions | yield ($TCID_{50}$/900 cm² roller bottle) |
|---|---|---|
| 0.1 | protein-free | $2.1 \times 10^{10}$ |
| 0.1 | +FCS | $6 \times 10^{9}$ |
| 0.05 | protein-free | $3.15 \times 10^{10}$ |
| 0.05 | +FCS | $2.1 \times 10^{10}$ |
| 0.001 | protein-free | $1.4 \times 10^{10}$ |
| 0.001 | +FCS | $1.6 \times 10^{10}$ |

EXAMPLE 17

Large-scale Production of Rotavirus in Protein-free VERO Cells in an Augmentation Loop System Rotaviruses are the most significant cause of severe gastroenteritis in young children and animals, particularly in piglets. Infection and disease in older children and adults also commonly occur. Rotaviruses are reviewed by Estes M. K. and Kapikian A. Z. and Chanock R. M. in Fields et al. (eds.) VIROLOGY, Vol. 2, Raven Press New York.

Rotaviruses are non-enveloped viruses with an inner and an outer shell. The outer capsid contains a hemagglutinin-like polypeptide (VP4) of which there exist at least 8 different variants. Similar to influenza virus, rotavirus requires a proteolytic enzyme for its amplification in culture cells. Proteolytic enzymes like trypsin enhance infectivity by cleavage of VP4. Yet, the protease concentrations necessary for efficient virus activation were high and had severe cytotoxic effects. Influenza virus and rotavirus also have in common that they change their serotypes frequently. Accordingly, the necessity emerges to have a powerful system for vaccine production that tolerates frequent switches to recent virus isolates. This requires a flexible system as it is provided by the present invention. Due to the physical separation of fermentation and activation steps, the activation can be specifically adapted to the requirements of the various serotypes.

For the large scale production of Rotavirus, a 2 liter fermenter of biomass cell culture of protein-free VERO cells was inoculated with 0.5 ml of human rotavirus type C and grown with continuous medium changes at 37° C. For the activation of non-infectious virus in an activation, portions of the medium containing the desired virus were continuously removed from the cell cultivation vessel to an activation vessel that contained pronase at a concentration of 50 μg/ml. Here, the virus was activated over a period of approximately one hour. The medium containing the pronase activated virus was then pumped into a vessel containing soy bean trypsin inhibitor for about one hour with a concentration sufficient to neutralize the residual pronase activity. The medium containing neutralized pronase with virus was then returned to the cell culture vessel for another round of replication. By continuous removal of the biomass cell culture medium from the fermenter and addition of fresh culture medium 5 l of virus containing medium was obtained during a time period of 3 days. The method of the invention allows activation of virus with much higher concentration of pronase than would be possible with conventional methods, where high concentrations of the protease would have cytopathic effects on the cell culture and hence on virus production, when incubated for such a long time span.

The description, tables and examples provided herein, while indicating preferred embodiments of the invention, are given by way of illustration and are not intended to limit the present invention. Various changes and modifications within the spirit and scope of the invention will become apparent to those skilled in the art upon reading the instant specification.

What is claimed is:

1. A method for producing a donor Orthomyxovirus for making reassortant viruses, comprising:
   (a) providing a culture of a continuous cell line of monkey kidney cells;
   (b) growing said cell for more than one generation in protein-free medium to ensure (i) adaptation of the cells to protein-free media and (ii) virus production capability;
   (c) infecting said culture of step (b) with a virus from the family of Orthomyxovirus;
   (d) selecting for ail Orthomyxovirus strain that exhibits a desired phenotype; and
   (e) isolating said donor Orthomyxovirus from step (d).

2. The method according to claim 1, wherein said desired phenotype is a high-yield phenotype or an attenuated virulence phenotype.

3. The method according to claim 1, wherein said virus is selected from the group of attenuated Influenza viruses, cold-adapted Influenza viruses, temperature-sensitive Influenza viruses, reassortant Influenza viruses, high yield donor Influenza viruses, wild-type Influenza viruses isolated from throat swabs of infected mammals and viruses that have been passaged in embryonated chicken eggs or cell culture adapted substrains of Influenza viruses.

4. The method of claim 1, wherein said cells are selected from the group consisting of VERO cells, CV-1 cells and LLC-MK2 cells.

5. A method of preventing or treating influenza infection, comprising:
   administering to a subject a vaccine obtainable by
   providing a culture of a continuous cell line of monkey kidney cells;

growing said cells for more than one generation in protein-free media to ensure (i) adaptation of the cells to protein-free media and (ii) virus production capability;

infecting said culture from the growing step with a virus from the family Orthomyxoviridae;

incubating said cell culture infected with said virus to propagate virus antigen into said medium;

harvesting said virus antigen from said culture; and preparing a vaccine with said harvested virus antigen.

6. A method for producing a reassortant Orthomyxovirus, comprising:

(a) providing a culture of a continuous cell line of monkey kidney cells;

(b) growing said cells for more than one generation in protein-free medium to ensure (i) adaptation of the cells to protein-free media and (ii) virus production capability;

(c) infecting said cells with a first Orthomyxovirus having a high-yield phenotype, and a second orthomyxovirus having at least one antigenic determinant;

(d) incubating said cell of step (b) to propagate said viruses and reassortants of said viruses, (e) selecting from said infected culture of step (d) a reassortant virus that comprises the high-yield phenotype from said first Orthomyxovirus and at least one antigenic determinant from said second Orthomyxovirus.

7. The method according to claim 6, wherein said Orthomyxovirus viruses are Influenza viruses.

8. The method according to claim 6, wherein step (c) employs an antibody that binds to antigenic determinants of said first virus but does not bind to antigenic determinants of said second virus.

9. The method according to claim 6, wherein said second Orthomyxovirus is designated for vaccine production.

10. The method according to claim 6, wherein said culture of monkey kidney cells are VERO cells.

11. A method fox producing a reassortant Orthomyxovirus, comprising:

(a) providing a culture of a continuous cell line of monkey kidney cells;

(b) growing said cells for more than one generation in protein-free medium to ensure (i) adaptation of the cells to protein-free media and (ii) virus production capability;

(c) infecting said cells with a first Orthomyxovirus having an attenuated virulence phenotype, and a second orthomyxovirus having at least one antigenic determinant;

(d) incubating said cells of step (b) to propagate said viruses and reassortants of said viruses, (e) selecting from said infected culture of step (d) a reassortant virus that comprises said attenuated virulence phenotype from said first Orthomyxovirus and at least one antigenic determinant from said second Orthomyxovirus.

12. The method according to claim 11, wherein said orthomyxovirus viruses are Influenza viruses.

13. The method according to claim 11, wherein step (c) employs an antibody that binds to antigenic determinants of said first virus but does not bind to antigenic determinants of said second virus.

14. The method according to claim 11, wherein said second Orthomyxovirus is designated for vaccine production.

15. The method according to claim 11, wherein said culture of monkey kidney cells are VERO cells.

16. A method for producing viral antigens acceptable for human administration, comprising:

(a) providing a culture of a continuous cell line of monkey kidney cells;

(b) growing said cells for more than one generation in protein-free medium to ensure (i) adaptation of the cells to protein-free media and (ii) virus production capability;

(c) infecting said culture of step (b) with a virus from the family Orthomyxoviridae; and (d) incubating said cell culture infected with said virus to propagate said virus into said medium to produce said viral antigens.

17. The method of claim 16, wherein the virus is an Influenza virus.

18. The method according to claim 16, wherein said culture of cells infected with said virus is contacted with at least one substance that augments the activation of said virus.

19. A method for producing influenza virus vaccine acceptable for human administration, comprising:

(a) providing a culture of a continuous cell line of monkey kidney cells;

(b) growing sail cells for more than one generation in protein-free media to ensure (i) adaptation of the cells to protein-free media and (ii) virus production capability;

(c) infecting said culture of step (b) with a virus from the family Orthomyxoviridae;

(d) incubating said cell culture infected with said virus to propagate virus antigen into said medium;

(e) harvesting said virus antigen from said culture; and (f) preparing a vaccine with said harvested virus antigen.

20. The method according to claim 19, wherein said cells are selected from the group of cell lines consisting of VERO, CV-1, and LLC-MK2 cell lines.

21. The method according to claim 20, wherein said cells are VERO cells.

22. A method for propagating influenza virus, comprising:

(a) providing a culture of a continuous cell line of monkey kidney cells;

(b) growing said cells for more than one generation in protein-free medium to ensure (i) adaptation of the cells to protein-free media and (ii) virus production capability;

(c) infecting said culture of step (b) with a virus from the family Orthomyxoviridae that has been isolated directly from an infected mammal; and (d) incubating said cell culture infected with said virus to propagate said virus.

23. The method according to claim 22, wherein the virus is an influenza virus.

24. The method according to claim 22, wherein said cells are selected from the croup of cell lines consisting of VERO, CV-1, and LLC-MK2 cell lines.

25. The method according to claim 22, wherein said cells are VERO cells.

26. The method according to claim 16, wherein during said step (b) said cells are grown for at least six generations.

27. The method according to claim 22, further comprising the step of contacting said cell culture of step (d) with at least one substance that augments the activation of said virus.

28. The method according to claim 16, wherein said cells are selected from the group consisting of VERO cells, CV-1 cells, and LLS-MK2 cell lines.

29. The method according to claim 28, wherein said cells are VERO cells.

30. The method according to claim 19, further comprising the step of contacting said cell culture of step (d) with at least one substance that augments the activation of said virus.

31. A method for producing Influenza virus antigen with mammalian Influenza virus having increased infectivity, wherein the antigen is suitable for human administration, comprising the steps of:
   (a) providing a culture comprising a continuous cell line of monkey kidney cells;
   (b) growing said cells in protein-free medium for more than one generation to ensure (i) adaptation of the cells to protein-free media and (ii) virus production capability;
   (c) infecting said culture with a mammalian strain of an Influenza virus that has a modified cleavage site in its hemagglutinin, wherein said modified cleavage site increases the susceptibility of said hemagglutinin to a substance that augments the activation of said virus; and
   (d) incubating said cell culture of step (c) to propagate said virus and thereby produce said Influenza virus antigen that is suitable for human administration.

32. A method for producing Influenza virus vaccine suitable for human administration, comprising the steps of:
   (a) providing a culture comprising a continuous cell line of monkey kidney cells;
   (b) growing said cells in protein-free medium for more than one generation to ensure (i) adaptation of the cells to protein-free media and (ii) virus production capability;
   (c) infecting said culture with a mammalian strain of an Influenza virus that has a modified cleavage site in its hemagglutinin, wherein said modified cleavage site increases the susceptibility of said hemagglutinin to a substance that augments the activation of said virus;
   (d) incubating said cell culture of step (c) to propagate said virus;
   (e) harvesting said virus; and
   (f) preparing a vaccine with the harvested virus, wherein the vaccine is suitable for human administration.

33. A method according to claim 32, wherein said monkey kidney cells selected from the group consisting of VERO cells, CV-1 cells, and LLC-MK2 cells.

34. A method according to claim 33, wherein said monkey kidney cells are VERO cells.

35. A method for the treatment of Influenza virus infection or for the prevention of Influenza virus infection comprising the step of administering to a human a vaccine obtainable by a method comprising the steps of:
   (a) providing a culture comprising a continuous cell line of monkey kidney cells;
   (b) growing said cells in protein-free medium for more than one generation to ensure (i) adaptation of the cells to protein-free media and (ii) virus production capability;
   (c) infecting said culture with a mammalian strain of an Influenza virus that has a modified cleavage site in its hemagglutinin, wherein said modified cleavage site increases the susceptibility of said hemagglutinin to a substance that augments the activation of said virus;
   (d) incubating said cell culture of step (c) to propagate said virus;
   (e) harvesting said virus; and
   (f) preparing a vaccine with the harvested virus, wherein the vaccine is suitable for human administration.

36. A method according to claim 35, wherein said monkey kidney cells selected from the group consisting of VERO cells, CV-1 cells, and LLC-MK2 cells.

37. A method according to claim 36, wherein said monkey kidney cells are VERO cells.

* * * * *